(12) United States Patent
Hoarau

(10) Patent No.: US 7,894,869 B2
(45) Date of Patent: Feb. 22, 2011

(54) MULTIPLE CONFIGURATION MEDICAL SENSOR AND TECHNIQUE FOR USING THE SAME

(75) Inventor: Carine Hoarau, Lafayette, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 691 days.

(21) Appl. No.: 11/716,770

(22) Filed: Mar. 9, 2007

(65) Prior Publication Data

US 2008/0221413 A1 Sep. 11, 2008

(51) Int. Cl.
*A61B 5/1455* (2006.01)
(52) U.S. Cl. ...................... 600/344; 600/323
(58) Field of Classification Search ............... 600/310, 600/322, 323, 344
See application file for complete search history.

(56) References Cited

U.S. PATENT DOCUMENTS

| | | | |
|---|---|---|---|
| 3,403,555 A | 10/1968 | Versaci et al. |
| 3,536,545 A | 10/1970 | Traynor et al. |
| D222,454 S | 10/1971 | Beeber |
| 3,721,813 A | 3/1973 | Condon et al. |
| 4,098,772 A | 7/1978 | Bonk et al. |
| D250,275 S | 11/1978 | Bond |
| D251,387 S | 3/1979 | Ramsay et al. |
| D262,488 S | 12/1981 | Rossman et al. |
| 4,334,544 A | 6/1982 | Hill et al. |
| 4,350,165 A | 9/1982 | Striese |
| 4,353,372 A | 10/1982 | Ayer |
| 4,380,240 A | 4/1983 | Jobsis et al. |
| 4,406,289 A | 9/1983 | Wesseling et al. |
| 4,510,551 A | 4/1985 | Brainard, II |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,677,528 A | 6/1987 | Miniet |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,722,120 A | 2/1988 | Lu |

(Continued)

FOREIGN PATENT DOCUMENTS

DE 3405444 8/1985

(Continued)

OTHER PUBLICATIONS

U.S. Appl. No. 11/507,814, filed Aug. 22, 2006, Baker et al.

(Continued)

*Primary Examiner*—Eric F Winakur
(74) *Attorney, Agent, or Firm*—Fletcher Yoder

(57) ABSTRACT

A sensor may be adapted to be placed on multiple tissue sites. A sensor is provided that may have one configuration associated with use on a digit and a second configuration associated with use on another tissue site, such as a forehead. Further, a sensor may be adapted to be a transmission-type sensor or a reflectance-type sensor, depending on its configuration.

43 Claims, 8 Drawing Sheets

U.S. PATENT DOCUMENTS

| | | |
|---|---|---|
| 4,726,382 A | 2/1988 | Boehmer et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,783,815 A | 11/1988 | Buttner |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jobsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hausman et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,039 A | 8/1991 | Hattori et al. |
| 5,041,187 A | 8/1991 | Hink et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,086,229 A | 2/1992 | Rosenthal et al. |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H001039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp, Jr. |
| 5,216,598 A | 6/1993 | Branstetter et al. |
| 5,217,012 A | 6/1993 | Young et al. |
| 5,217,013 A | 6/1993 | Lewis et al. |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,278,627 A | 1/1994 | Aoyagi et al. |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub |
| 5,348,005 A | 9/1994 | Merrick et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |

| | | | | | |
|---|---|---|---|---|---|
| 5,353,799 A | 10/1994 | Chance | 5,588,425 A | 12/1996 | Sackner et al. |
| 5,355,880 A | 10/1994 | Thomas et al. | 5,588,427 A | 12/1996 | Tien |
| 5,355,882 A | 10/1994 | Ukawa et al. | 5,590,652 A | 1/1997 | Inai |
| 5,361,758 A | 11/1994 | Hall et al. | 5,595,176 A | 1/1997 | Yamaura |
| 5,365,066 A | 11/1994 | Krueger, Jr. et al. | 5,596,986 A | 1/1997 | Goldfarb |
| 5,368,025 A | 11/1994 | Young et al. | 5,611,337 A | 3/1997 | Bukta |
| 5,368,026 A | 11/1994 | Swedlow et al. | 5,617,852 A | 4/1997 | MacGregor |
| 5,368,224 A | 11/1994 | Richardson et al. | 5,619,991 A | 4/1997 | Sloane |
| 5,372,136 A | 12/1994 | Steuer et al. | 5,619,992 A | 4/1997 | Guthrie et al. |
| 5,377,675 A | 1/1995 | Ruskewicz et al. | 5,626,140 A | 5/1997 | Feldman et al. |
| 5,385,143 A | 1/1995 | Aoyagi | 5,629,992 A | 5/1997 | Amersfoort et al. |
| 5,387,122 A | 2/1995 | Goldberger et al. | 5,630,413 A | 5/1997 | Thomas et al. |
| 5,390,670 A | 2/1995 | Centa et al. | 5,632,272 A | 5/1997 | Diab et al. |
| 5,392,777 A | 2/1995 | Swedlow et al. | 5,632,273 A | 5/1997 | Suzuki |
| 5,398,680 A | 3/1995 | Polson et al. | 5,634,459 A | 6/1997 | Gardosi |
| 5,402,777 A | 4/1995 | Warring et al. | 5,638,593 A | 6/1997 | Gerhardt et al. |
| 5,402,779 A | 4/1995 | Chen et al. | 5,638,816 A | 6/1997 | Kiani-Azarbayjany et al. |
| 5,411,023 A | 5/1995 | Morris, Sr. et al. | 5,638,818 A | 6/1997 | Diab et al. |
| 5,411,024 A | 5/1995 | Thomas et al. | 5,645,060 A | 7/1997 | Yorkey |
| 5,413,099 A | 5/1995 | Schmidt et al. | 5,645,440 A | 7/1997 | Tobler et al. |
| 5,413,100 A | 5/1995 | Barthelemy et al. | 5,660,567 A | 8/1997 | Nierlich et al. |
| 5,413,101 A | 5/1995 | Sugiura | 5,662,105 A | 9/1997 | Tien |
| 5,413,102 A | 5/1995 | Schmidt et al. | 5,662,106 A | 9/1997 | Swedlow et al. |
| 5,417,207 A | 5/1995 | Young et al. | 5,664,270 A | 9/1997 | Bell et al. |
| 5,421,329 A | 6/1995 | Casciani et al. | 5,666,952 A | 9/1997 | Fuse et al. |
| 5,425,360 A | 6/1995 | Nelson | 5,671,529 A | 9/1997 | Nelson |
| 5,425,362 A | 6/1995 | Siker et al. | 5,673,692 A | 10/1997 | Schulze et al. |
| 5,427,093 A | 6/1995 | Ogawa et al. | 5,673,693 A | 10/1997 | Solenberger |
| 5,429,128 A | 7/1995 | Cadell et al. | 5,676,139 A | 10/1997 | Goldberger et al. |
| 5,429,129 A | 7/1995 | Lovejoy et al. | 5,676,141 A | 10/1997 | Hollub |
| 5,431,159 A | 7/1995 | Baker et al. | 5,678,544 A | 10/1997 | DeLonzor et al. |
| 5,431,170 A | 7/1995 | Mathews | 5,680,857 A | 10/1997 | Pelikan et al. |
| 5,437,275 A | 8/1995 | Amundsen et al. | 5,685,299 A | 11/1997 | Diab et al. |
| 5,438,986 A | 8/1995 | Disch et al. | 5,685,301 A | 11/1997 | Klomhaus |
| 5,448,991 A | 9/1995 | Polson et al. | 5,687,719 A | 11/1997 | Sato et al. |
| 5,452,717 A | 9/1995 | Branigan et al. | 5,687,722 A | 11/1997 | Tien et al. |
| 5,465,714 A | 11/1995 | Scheuing | 5,692,503 A | 12/1997 | Kuenstner |
| 5,469,845 A | 11/1995 | DeLonzor et al. | 5,692,505 A | 12/1997 | Fouts |
| RE35,122 E | 12/1995 | Corenman et al. | 5,709,205 A | 1/1998 | Bukta |
| 5,482,034 A | 1/1996 | Lewis et al. | 5,713,355 A | 2/1998 | Richardson et al. |
| 5,482,036 A | 1/1996 | Diab et al. | 5,724,967 A | 3/1998 | Venkatachalam |
| 5,485,847 A | 1/1996 | Baker, Jr. | 5,727,547 A | 3/1998 | Levinson et al. |
| 5,490,505 A | 2/1996 | Diab et al. | 5,730,124 A | 3/1998 | Yamauchi |
| 5,490,523 A | 2/1996 | Isaacson et al. | 5,731,582 A | 3/1998 | West |
| 5,491,299 A | 2/1996 | Naylor et al. | D393,830 S | 4/1998 | Tobler et al. |
| 5,494,032 A | 2/1996 | Robinson et al. | 5,743,260 A | 4/1998 | Chung et al. |
| 5,494,043 A | 2/1996 | O'Sullivan et al. | 5,743,262 A | 4/1998 | Lepper, Jr. et al. |
| 5,497,771 A | 3/1996 | Rosenheimer | 5,743,263 A | 4/1998 | Baker, Jr. |
| 5,499,627 A | 3/1996 | Steuer et al. | 5,746,206 A | 5/1998 | Mannheimer |
| 5,503,148 A | 4/1996 | Pologe et al. | 5,746,697 A | 5/1998 | Swedlow et al. |
| 5,505,199 A | 4/1996 | Kim | 5,752,914 A | 5/1998 | Delonzor et al. |
| 5,507,286 A | 4/1996 | Solenberger | 5,755,226 A | 5/1998 | Carim et al. |
| 5,511,546 A | 4/1996 | Hon | 5,758,644 A | 6/1998 | Diab et al. |
| 5,517,988 A | 5/1996 | Gerhard | 5,760,910 A | 6/1998 | Lepper, Jr. et al. |
| 5,520,177 A | 5/1996 | Ogawa et al. | 5,766,125 A | 6/1998 | Aoyagi et al. |
| 5,521,851 A | 5/1996 | Wei et al. | 5,766,127 A | 6/1998 | Pologe et al. |
| 5,522,388 A | 6/1996 | Ishikawa et al. | 5,769,785 A | 6/1998 | Diab et al. |
| 5,524,617 A | 6/1996 | Mannheimer | 5,772,587 A | 6/1998 | Gratton et al. |
| 5,529,064 A | 6/1996 | Rall et al. | 5,774,213 A | 6/1998 | Trebino et al. |
| 5,533,507 A | 7/1996 | Potratz | 5,776,058 A | 7/1998 | Levinson et al. |
| 5,551,423 A | 9/1996 | Sugiura | 5,776,059 A | 7/1998 | Kaestle et al. |
| 5,551,424 A | 9/1996 | Morrison et al. | 5,779,630 A | 7/1998 | Fein et al. |
| 5,553,614 A | 9/1996 | Chance | 5,779,631 A | 7/1998 | Chance |
| 5,553,615 A | 9/1996 | Carim et al. | 5,782,237 A | 7/1998 | Casciani et al. |
| 5,555,882 A | 9/1996 | Richardson et al. | 5,782,756 A | 7/1998 | Mannheimer |
| 5,558,096 A | 9/1996 | Palatnik | 5,782,757 A | 7/1998 | Diab et al. |
| 5,560,355 A | 10/1996 | Merchant et al. | 5,782,758 A | 7/1998 | Ausec et al. |
| 5,564,417 A | 10/1996 | Chance | 5,786,592 A | 7/1998 | Hok |
| 5,575,284 A | 11/1996 | Athan et al. | 5,788,634 A | 8/1998 | Suda et al. |
| 5,575,285 A | 11/1996 | Takanashi et al. | 5,790,729 A | 8/1998 | Pologe et al. |
| 5,577,500 A | 11/1996 | Potratz | 5,792,052 A | 8/1998 | Isaacson et al. |
| 5,582,169 A | 12/1996 | Oda et al. | 5,795,292 A | 8/1998 | Lewis et al. |
| 5,584,296 A | 12/1996 | Cui et al. | 5,797,841 A | 8/1998 | Delonzor et al. |

| | | | | | | |
|---|---|---|---|---|---|---|
| 5,800,348 A | 9/1998 | Kaestle | | 5,995,855 A | 11/1999 | Kiani et al. |
| 5,800,349 A | 9/1998 | Isaacson et al. | | 5,995,856 A | 11/1999 | Mannheimer et al. |
| 5,803,910 A | 9/1998 | Potratz | | 5,995,858 A | 11/1999 | Kinast |
| 5,807,246 A | 9/1998 | Sakaguchi et al. | | 5,995,859 A | 11/1999 | Takahashi |
| 5,807,247 A | 9/1998 | Merchant et al. | | 5,997,343 A | 12/1999 | Mills et al. |
| 5,807,248 A | 9/1998 | Mills | | 5,999,834 A | 12/1999 | Wang et al. |
| 5,810,723 A | 9/1998 | Aldrich | | 6,002,952 A | 12/1999 | Diab et al. |
| 5,810,724 A | 9/1998 | Gronvall | | 6,005,658 A | 12/1999 | Kaluza et al. |
| 5,813,980 A | 9/1998 | Levinson et al. | | 6,006,120 A | 12/1999 | Levin |
| 5,817,008 A | 10/1998 | Rafert et al. | | 6,011,985 A | 1/2000 | Athan et al. |
| 5,817,009 A | 10/1998 | Rosenheimer et al. | | 6,011,986 A | 1/2000 | Diab et al. |
| 5,817,010 A | 10/1998 | Hibl | | 6,014,576 A | 1/2000 | Raley |
| 5,818,985 A | 10/1998 | Merchant et al. | | 6,018,673 A | 1/2000 | Chin et al. |
| 5,820,550 A | 10/1998 | Polson et al. | | 6,018,674 A | 1/2000 | Aronow |
| 5,823,950 A | 10/1998 | Diab et al. | | 6,022,321 A | 2/2000 | Amano et al. |
| 5,823,952 A | 10/1998 | Levinson et al. | | 6,023,541 A | 2/2000 | Merchant et al. |
| 5,827,179 A | 10/1998 | Lichter et al. | | 6,026,312 A | 2/2000 | Shemwell et al. |
| 5,827,182 A | 10/1998 | Raley et al. | | 6,026,314 A | 2/2000 | Amerov et al. |
| 5,829,439 A | 11/1998 | Yokosawa et al. | | 6,031,603 A | 2/2000 | Fine et al. |
| 5,830,135 A | 11/1998 | Bosque et al. | | 6,035,223 A | 3/2000 | Baker, Jr. |
| 5,830,136 A | 11/1998 | Delonzor et al. | | 6,036,642 A | 3/2000 | Diab et al. |
| 5,830,137 A | 11/1998 | Scharf | | 6,041,247 A | 3/2000 | Weckstrom et al. |
| 5,839,439 A | 11/1998 | Nierlich et al. | | 6,044,283 A | 3/2000 | Fein et al. |
| RE36,000 E | 12/1998 | Swedlow et al. | | 6,047,201 A | 4/2000 | Jackson, III |
| 5,842,979 A | 12/1998 | Jarman | | 6,055,447 A | 4/2000 | Weil et al. |
| 5,842,981 A | 12/1998 | Larsen et al. | | 6,061,584 A | 5/2000 | Lovejoy et al. |
| 5,842,982 A | 12/1998 | Mannheimer | | 6,064,898 A | 5/2000 | Aldrich |
| 5,846,190 A | 12/1998 | Woehrle | | 6,064,899 A | 5/2000 | Fein et al. |
| 5,851,178 A | 12/1998 | Aronow | | 6,067,462 A | 5/2000 | Diab et al. |
| 5,851,179 A | 12/1998 | Ritson et al. | | 6,073,038 A | 6/2000 | Wang et al. |
| 5,853,364 A | 12/1998 | Baker, Jr. et al. | | 6,078,829 A | 6/2000 | Uchida et al. |
| 5,860,919 A | 1/1999 | Kiani-Azarbayjany et al. | | 6,078,833 A | 6/2000 | Hueber |
| 5,865,736 A | 2/1999 | Baker, Jr. et al. | | 6,081,735 A | 6/2000 | Diab et al. |
| 5,879,294 A | 3/1999 | Anderson et al. | | 6,083,157 A | 7/2000 | Noller |
| 5,885,213 A | 3/1999 | Richardson et al. | | 6,083,172 A | 7/2000 | Baker, Jr. et al. |
| 5,890,929 A | 4/1999 | Mills et al. | | 6,088,607 A | 7/2000 | Diab et al. |
| 5,891,021 A | 4/1999 | Dillon et al. | | 6,094,592 A | 7/2000 | Yorkey et al. |
| 5,891,022 A | 4/1999 | Pologe | | 6,095,974 A | 8/2000 | Shemwell et al. |
| 5,891,024 A | 4/1999 | Jarman et al. | | 6,104,938 A | 8/2000 | Huiku et al. |
| 5,891,025 A | 4/1999 | Buschmann et al. | | 6,104,939 A | 8/2000 | Groner et al. |
| 5,891,026 A | 4/1999 | Wang et al. | | 6,112,107 A | 8/2000 | Hannula |
| 5,902,235 A | 5/1999 | Lewis et al. | | 6,113,541 A | 9/2000 | Dias et al. |
| 5,910,108 A | 6/1999 | Solenberger | | 6,115,621 A | 9/2000 | Chin |
| 5,911,690 A | 6/1999 | Rall | | 6,122,535 A | 9/2000 | Kaestle et al. |
| 5,912,656 A | 6/1999 | Tham et al. | | 6,133,994 A | 10/2000 | Mathews et al. |
| 5,913,819 A | 6/1999 | Taylor et al. | | 6,135,952 A | 10/2000 | Coetzee |
| 5,916,154 A | 6/1999 | Hobbs et al. | | 6,144,444 A | 11/2000 | Haworth et al. |
| 5,916,155 A | 6/1999 | Levinson et al. | | 6,144,867 A | 11/2000 | Walker et al. |
| 5,919,133 A | 7/1999 | Taylor et al. | | 6,144,868 A | 11/2000 | Parker |
| 5,919,134 A | 7/1999 | Diab | | 6,147,850 A | 11/2000 | Gronowicz, Jr. et al. |
| 5,920,263 A | 7/1999 | Huttenhoff et al. | | 6,149,481 A | 11/2000 | Wang et al. |
| 5,921,921 A | 7/1999 | Potratz et al. | | 6,151,107 A | 11/2000 | Schollermann et al. |
| 5,922,607 A | 7/1999 | Bernreuter | | 6,151,516 A | 11/2000 | Kiani-Azarbayjany et al. |
| 5,924,979 A | 7/1999 | Swedlow et al. | | 6,151,518 A | 11/2000 | Hayashi |
| 5,924,980 A | 7/1999 | Coetzee | | 6,152,754 A | 11/2000 | Gerhardt et al. |
| 5,924,982 A | 7/1999 | Chin | | 6,154,667 A | 11/2000 | Miura et al. |
| 5,924,985 A | 7/1999 | Jones | | 6,159,147 A | 12/2000 | Lichter et al. |
| 5,934,277 A | 8/1999 | Mortz | | 6,163,175 A | 12/2000 | Sharpe-Geisler |
| 5,934,925 A | 8/1999 | Tobler et al. | | 6,163,715 A | 12/2000 | Larsen et al. |
| 5,940,182 A | 8/1999 | Lepper, Jr. et al. | | 6,165,005 A | 12/2000 | Mills et al. |
| 5,954,644 A | 9/1999 | Dettling et al. | | 6,173,196 B1 | 1/2001 | Delonzor et al. |
| 5,957,840 A | 9/1999 | Terasawa et al. | | 6,178,343 B1 | 1/2001 | Bindszus et al. |
| 5,960,610 A | 10/1999 | Levinson et al. | | 6,179,159 B1 | 1/2001 | Gurley |
| 5,961,450 A | 10/1999 | Merchant et al. | | 6,181,958 B1 | 1/2001 | Steuer et al. |
| 5,961,452 A | 10/1999 | Chung et al. | | 6,181,959 B1 | 1/2001 | Schollermann et al. |
| 5,964,701 A | 10/1999 | Asada et al. | | 6,184,521 B1 | 2/2001 | Coffin, IV et al. |
| 5,971,930 A | 10/1999 | Elghazzawi | | 6,188,470 B1 | 2/2001 | Grace |
| 5,978,691 A | 11/1999 | Mills | | 6,192,260 B1 | 2/2001 | Chance |
| 5,978,693 A | 11/1999 | Hamilton et al. | | 6,195,575 B1 | 2/2001 | Levinson |
| 5,983,120 A | 11/1999 | Groner et al. | | 6,198,951 B1 | 3/2001 | Kosuda et al. |
| 5,983,122 A | 11/1999 | Jarman et al. | | 6,206,830 B1 | 3/2001 | Diab et al. |
| 5,987,343 A | 11/1999 | Kinast | | 6,213,952 B1 | 4/2001 | Finarov et al. |
| 5,991,648 A | 11/1999 | Levin | | 6,217,523 B1 | 4/2001 | Amano et al. |

| | | | | | | |
|---|---|---|---|---|---|---|
| 6,222,189 B1 | 4/2001 | Misner et al. | | 6,438,399 B1 | 8/2002 | Kurth |
| 6,223,064 B1 | 4/2001 | Lynn et al. | | 6,449,501 B1 | 9/2002 | Reuss |
| 6,226,539 B1 | 5/2001 | Potratz | | 6,453,183 B1 | 9/2002 | Walker |
| 6,226,540 B1 | 5/2001 | Bernreuter | | 6,453,184 B1 | 9/2002 | Hyogo et al. |
| 6,229,856 B1 | 5/2001 | Diab et al. | | 6,456,862 B2 | 9/2002 | Benni |
| 6,230,035 B1 | 5/2001 | Aoyagi et al. | | 6,461,305 B1 | 10/2002 | Schnall |
| 6,233,470 B1 | 5/2001 | Tsuchiya | | 6,463,310 B1 | 10/2002 | Swedlow et al. |
| 6,236,871 B1 | 5/2001 | Tsuchiya | | 6,463,311 B1 | 10/2002 | Diab |
| 6,236,872 B1 | 5/2001 | Diab et al. | | 6,466,808 B1 | 10/2002 | Chin et al. |
| 6,240,305 B1 | 5/2001 | Tsuchiya | | 6,466,809 B1 | 10/2002 | Riley |
| 6,253,097 B1 | 6/2001 | Aronow et al. | | 6,470,199 B1 | 10/2002 | Kopotic et al. |
| 6,253,098 B1 | 6/2001 | Walker et al. | | 6,470,200 B2 | 10/2002 | Walker et al. |
| 6,256,523 B1 | 7/2001 | Diab et al. | | 6,480,729 B2 | 11/2002 | Stone |
| 6,256,524 B1 | 7/2001 | Walker et al. | | 6,490,466 B1 | 12/2002 | Chew et al. |
| 6,261,236 B1 | 7/2001 | Grimblatov | | 6,493,568 B1 | 12/2002 | Bell et al. |
| 6,263,221 B1 | 7/2001 | Chance et al. | | 6,496,711 B1 | 12/2002 | Athan et al. |
| 6,263,222 B1 | 7/2001 | Diab et al. | | 6,498,942 B1 | 12/2002 | Esenaliev et al. |
| 6,263,223 B1 | 7/2001 | Shepherd et al. | | 6,501,974 B2 | 12/2002 | Huiku |
| 6,266,546 B1 | 7/2001 | Steuer et al. | | 6,501,975 B2 | 12/2002 | Diab et al. |
| 6,266,547 B1 | 7/2001 | Walker et al. | | 6,505,060 B1 | 1/2003 | Norris |
| 6,272,363 B1 | 8/2001 | Casciani et al. | | 6,505,061 B2 | 1/2003 | Larson |
| 6,278,522 B1 | 8/2001 | Lepper, Jr. et al. | | 6,505,133 B1 | 1/2003 | Hanna et al. |
| 6,280,213 B1 | 8/2001 | Tobler et al. | | 6,510,329 B2 | 1/2003 | Heckel |
| 6,280,381 B1 | 8/2001 | Malin et al. | | 6,510,331 B1 | 1/2003 | Williams et al. |
| 6,285,894 B1 | 9/2001 | Oppelt et al. | | 6,512,937 B2 | 1/2003 | Blank et al. |
| 6,285,895 B1 | 9/2001 | Ristolainen et al. | | 6,515,273 B2 | 2/2003 | Al-Ali |
| 6,285,896 B1 | 9/2001 | Tobler et al. | | 6,519,484 B1 | 2/2003 | Lovejoy et al. |
| 6,298,252 B1 | 10/2001 | Kovach et al. | | 6,519,486 B1 | 2/2003 | Edgar, Jr. et al. |
| 6,308,089 B1 | 10/2001 | von der Ruhr et al. | | 6,519,487 B1 | 2/2003 | Parker |
| 6,321,100 B1 | 11/2001 | Parker | | 6,525,386 B1 | 2/2003 | Mills et al. |
| 6,330,468 B1 | 12/2001 | Scharf | | 6,526,300 B1 | 2/2003 | Kiani et al. |
| 6,334,065 B1 | 12/2001 | Al-Ali et al. | | 6,526,301 B2 | 2/2003 | Larsen et al. |
| 6,339,715 B1 | 1/2002 | Bahr et al. | | 6,541,756 B2 | 4/2003 | Schulz et al. |
| 6,342,039 B1 | 1/2002 | Lynn et al. | | 6,542,764 B1 | 4/2003 | Al-Ali et al. |
| 6,343,223 B1 | 1/2002 | Chin et al. | | 6,546,267 B1 | 4/2003 | Sugiura et al. |
| 6,343,224 B1 | 1/2002 | Parker | | 6,553,241 B2 | 4/2003 | Mannheimer et al. |
| 6,349,228 B1 | 2/2002 | Kiani et al. | | 6,553,242 B1 | 4/2003 | Sarussi |
| 6,351,658 B1 | 2/2002 | Middleman et al. | | 6,553,243 B2 | 4/2003 | Gurley |
| 6,353,750 B1 | 3/2002 | Kimura et al. | | 6,554,788 B1 | 4/2003 | Hunley et al. |
| 6,356,774 B1 | 3/2002 | Bernstein et al. | | 6,556,852 B1 | 4/2003 | Schulze et al. |
| 6,360,113 B1 | 3/2002 | Dettling | | 6,560,470 B1 | 5/2003 | Pologe |
| 6,360,114 B1 | 3/2002 | Diab et al. | | 6,564,077 B2 | 5/2003 | Mortara |
| 6,361,501 B1 | 3/2002 | Amano et al. | | 6,564,088 B1 | 5/2003 | Soller et al. |
| 6,363,269 B1 | 3/2002 | Hanna et al. | | 6,571,113 B1 | 5/2003 | Fein et al. |
| D455,834 S | 4/2002 | Donars et al. | | 6,571,114 B1 | 5/2003 | Koike et al. |
| 6,370,408 B1 | 4/2002 | Merchant et al. | | 6,574,491 B2 | 6/2003 | Elghazzawi |
| 6,370,409 B1 | 4/2002 | Chung et al. | | 6,580,086 B1 | 6/2003 | Schulz et al. |
| 6,371,921 B1 | 4/2002 | Caro et al. | | 6,584,336 B1 | 6/2003 | Ali et al. |
| 6,374,129 B1 | 4/2002 | Chin et al. | | 6,587,703 B2 | 7/2003 | Cheng et al. |
| 6,377,829 B1 | 4/2002 | Al-Ali | | 6,587,704 B1 | 7/2003 | Fine et al. |
| 6,381,479 B1 | 4/2002 | Norris | | 6,589,172 B2 | 7/2003 | Williams et al. |
| 6,381,480 B1 | 4/2002 | Stoddart et al. | | 6,591,122 B2 | 7/2003 | Schmitt |
| 6,385,471 B1 | 5/2002 | Mortz | | 6,591,123 B2 | 7/2003 | Fein et al. |
| 6,385,821 B1 | 5/2002 | Modgil et al. | | 6,594,511 B2 | 7/2003 | Stone et al. |
| 6,388,240 B2 | 5/2002 | Schulz et al. | | 6,594,512 B2 | 7/2003 | Huang |
| 6,393,310 B1 | 5/2002 | Kuenstner | | 6,594,513 B1 | 7/2003 | Jobsis et al. |
| 6,393,311 B1 | 5/2002 | Edgar, Jr. et al. | | 6,597,931 B1 | 7/2003 | Cheng et al. |
| 6,397,091 B2 | 5/2002 | Diab et al. | | 6,597,933 B2 | 7/2003 | Kiani et al. |
| 6,397,092 B1 | 5/2002 | Norris et al. | | 6,600,940 B1 | 7/2003 | Fein et al. |
| 6,397,093 B1 | 5/2002 | Aldrich | | 6,606,510 B2 | 8/2003 | Swedlow et al. |
| 6,400,971 B1 | 6/2002 | Finarov et al. | | 6,606,511 B1 | 8/2003 | Ali et al. |
| 6,400,972 B1 | 6/2002 | Fine | | 6,606,512 B2 | 8/2003 | Muz et al. |
| 6,400,973 B1 | 6/2002 | Winter | | 6,608,562 B1 | 8/2003 | Kimura et al. |
| 6,402,690 B1 | 6/2002 | Rhee et al. | | 6,609,016 B1 | 8/2003 | Lynn |
| 6,408,198 B1 | 6/2002 | Hanna et al. | | 6,615,064 B1 | 9/2003 | Aldrich |
| 6,411,832 B1 | 6/2002 | Guthermann | | 6,615,065 B1 | 9/2003 | Barrett et al. |
| 6,411,833 B1 | 6/2002 | Baker, Jr. et al. | | 6,618,602 B2 | 9/2003 | Levin |
| 6,421,549 B1 | 7/2002 | Jacques | | 6,622,034 B1 | 9/2003 | Gorski et al. |
| 6,430,423 B2 | 8/2002 | DeLonzor et al. | | 6,628,975 B1 | 9/2003 | Fein et al. |
| 6,430,513 B1 | 8/2002 | Wang et al. | | 6,631,281 B1 | 10/2003 | Kästle |
| 6,430,525 B1 | 8/2002 | Weber et al. | | 6,632,181 B2 | 10/2003 | Flaherty et al. |
| 6,434,408 B1 | 8/2002 | Heckel | | 6,640,116 B2 | 10/2003 | Diab |
| 6,438,396 B1 | 8/2002 | Cook et al. | | 6,643,530 B2 | 11/2003 | Diab et al. |

| | | |
|---|---|---|
| 6,643,531 B1 | 11/2003 | Katarow |
| 6,647,279 B2 | 11/2003 | Pologe |
| 6,647,280 B2 | 11/2003 | Bahr et al. |
| 6,650,916 B2 | 11/2003 | Cook et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Pishney et al. |
| 6,658,277 B2 | 12/2003 | Wasserman |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,712,762 B1 | 3/2004 | Lichter et al. |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,962 B1 | 5/2004 | Katarow et al. |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | Chin et al. |
| 6,754,515 B1 | 6/2004 | Pologe |
| 6,754,516 B2 | 6/2004 | Mannheimer |
| 6,760,607 B2 | 7/2004 | Al-All |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckström |
| 6,792,300 B1 | 9/2004 | Diab et al. |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,898,452 B2 | 5/2005 | Al-Ali et al. |
| 6,909,912 B2 | 6/2005 | Melker |
| 6,912,413 B2 | 6/2005 | Rantala et al. |
| 6,920,345 B2 | 7/2005 | Al-Ali et al. |
| 6,931,269 B2 | 8/2005 | Terry |
| 6,934,570 B2 | 8/2005 | Kiani et al. |
| 6,941,162 B2 | 9/2005 | Fudge et al. |
| 6,947,781 B2 | 9/2005 | Asada et al. |
| 6,950,687 B2 | 9/2005 | Al-Ali |
| 6,954,664 B2 | 10/2005 | Sweitzer et al. |
| 6,968,221 B2 | 11/2005 | Rosenthal |
| 6,979,812 B2 | 12/2005 | Al-Ali |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Okita et al. |
| 6,992,772 B2 | 1/2006 | Block |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B2 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali |
| 7,027,850 B2 | 4/2006 | Wasserman |
| 7,039,449 B2 | 5/2006 | Al-Ali |
| 7,043,289 B2 | 5/2006 | Fine et al. |
| 7,047,055 B2 | 5/2006 | Boas et al. |
| 7,060,035 B2 | 6/2006 | Wasserman |
| 7,062,307 B2 | 6/2006 | Norris et al. |
| 7,067,893 B2 | 6/2006 | Mills et al. |
| 7,072,701 B2 | 7/2006 | Chen et al. |

| | | | | | | |
|---|---|---|---|---|---|---|
| 7,072,702 B2 | 7/2006 | Edgar, Jr. et al. | | 2004/0204637 A1 | 10/2004 | Diab et al. |
| 7,079,880 B2 | 7/2006 | Stetson | | 2004/0204638 A1 | 10/2004 | Diab et al. |
| 7,085,597 B2 | 8/2006 | Fein et al. | | 2004/0204639 A1 | 10/2004 | Casciani et al. |
| 7,096,052 B2 | 8/2006 | Mason et al. | | 2004/0204865 A1 | 10/2004 | Lee et al. |
| 7,096,054 B2 | 8/2006 | Abdul-Hafiz et al. | | 2004/0210146 A1 | 10/2004 | Diab et al. |
| 7,107,088 B2 | 9/2006 | Aceti | | 2004/0215085 A1 | 10/2004 | Schnall |
| 7,113,815 B2 | 9/2006 | O'Neil et al. | | 2004/0236196 A1 | 11/2004 | Diab et al. |
| 7,123,950 B2 | 10/2006 | Mannheimer | | 2005/0004479 A1 | 1/2005 | Townsend et al. |
| 7,127,278 B2 | 10/2006 | Melker et al. | | 2005/0014999 A1 | 1/2005 | Rahe-Meyer |
| 7,130,671 B2 | 10/2006 | Baker, Jr. et al. | | 2005/0020887 A1 | 1/2005 | Goldberg |
| 7,132,641 B2 | 11/2006 | Schulz et al. | | 2005/0033131 A1 | 2/2005 | Chen et al. |
| 7,133,711 B2 | 11/2006 | Chernoguz et al. | | 2005/0043599 A1 | 2/2005 | O'Mara |
| 7,139,559 B2 | 11/2006 | Kenagy et al. | | 2005/0043600 A1 | 2/2005 | Diab et al. |
| 7,142,901 B2 | 11/2006 | Kiani et al. | | 2005/0049468 A1 | 3/2005 | Carlson et al. |
| 7,162,288 B2 | 1/2007 | Nordstrom et al. | | 2005/0070733 A1 | 3/2005 | Sigl et al. |
| 7,190,987 B2 | 3/2007 | Lindekugel et al. | | 2005/0070773 A1 | 3/2005 | Chin et al. |
| 7,198,778 B2 | 4/2007 | Achilefu et al. | | 2005/0075546 A1 | 4/2005 | Samsoondar et al. |
| 7,215,984 B2 | 5/2007 | Diab et al. | | 2005/0075550 A1 | 4/2005 | Lindekugel |
| 7,228,161 B2 | 6/2007 | Chin | | 2005/0085704 A1 | 4/2005 | Schulz et al. |
| 7,236,881 B2 | 6/2007 | Liu et al. | | 2005/0090720 A1 | 4/2005 | Wu et al. |
| 7,248,910 B2 | 7/2007 | Li et al. | | 2005/0197548 A1 | 9/2005 | Dietiker |
| 7,254,433 B2 | 8/2007 | Diab et al. | | 2005/0228248 A1 | 10/2005 | Dietiker |
| 7,254,434 B2 | 8/2007 | Schulz et al. | | 2005/0256386 A1 | 11/2005 | Chan et al. |
| 7,255,006 B2 | 8/2007 | Spanke et al. | | 2005/0272986 A1 | 12/2005 | Smith et al. |
| 7,272,425 B2 | 9/2007 | Al-Ali | | 2005/0277819 A1 | 12/2005 | Kiani et al. |
| 7,280,858 B2 | 10/2007 | Al-Ali et al. | | 2006/0020179 A1 | 1/2006 | Anderson et al. |
| 7,292,150 B2 | 11/2007 | Shaw | | 2006/0030764 A1 | 2/2006 | Porges et al. |
| 7,295,866 B2 | 11/2007 | Al-Ali | | 2006/0058594 A1 | 3/2006 | Ishizuka et al. |
| 7,305,262 B2 | 12/2007 | Brodnick et al. | | 2006/0074280 A1 | 4/2006 | Martis et al. |
| 7,315,753 B2 | 1/2008 | Baker, Jr. et al. | | 2006/0084852 A1 | 4/2006 | Mason et al. |
| 7,341,559 B2 * | 3/2008 | Schulz et al. ............... 600/309 | | 2006/0084878 A1 | 4/2006 | Banet et al. |
| 2002/0016537 A1 | 2/2002 | Muz et al. | | 2006/0089547 A1 | 4/2006 | Sarussi |
| 2002/0026109 A1 | 2/2002 | Diab et al. | | 2006/0106294 A1 | 5/2006 | Maser et al. |
| 2002/0028990 A1 | 3/2002 | Shepherd et al. | | 2006/0122517 A1 | 6/2006 | Banet et al. |
| 2002/0038078 A1 | 3/2002 | Ito | | 2006/0129039 A1 | 6/2006 | Lindner et al. |
| 2002/0042558 A1 | 4/2002 | Mendelson | | 2006/0155198 A1 | 7/2006 | Schmid |
| 2002/0068859 A1 | 6/2002 | Knopp | | 2006/0173257 A1 | 8/2006 | Nagai et al. |
| 2002/0072681 A1 | 6/2002 | Schnali | | 2006/0200018 A1 | 9/2006 | Al-Ali |
| 2002/0116797 A1 | 8/2002 | Modgil et al. | | 2007/0032710 A1 | 2/2007 | Raridan et al. |
| 2002/0128544 A1 | 9/2002 | Diab et al. | | 2007/0032712 A1 | 2/2007 | Raridan et al. |
| 2002/0133067 A1 | 9/2002 | Jackson, III | | 2007/0032715 A1 | 2/2007 | Eghbal et al. |
| 2002/0156354 A1 | 10/2002 | Larson | | 2007/0060808 A1 | 3/2007 | Hoarau |
| 2002/0173706 A1 | 11/2002 | Takatani | | 2007/0073117 A1 | 3/2007 | Raridan |
| 2002/0190863 A1 | 12/2002 | Lynn | | 2007/0073121 A1 | 3/2007 | Hoarau et al. |
| 2003/0018243 A1 | 1/2003 | Gerhardt et al. | | 2007/0073122 A1 | 3/2007 | Hoarau |
| 2003/0036690 A1 | 2/2003 | Geddes et al. | | 2007/0073123 A1 | 3/2007 | Raridan |
| 2003/0045785 A1 | 3/2003 | Diab et al. | | 2007/0073125 A1 | 3/2007 | Hoarau et al. |
| 2003/0073889 A1 | 4/2003 | Keilbach et al. | | 2007/0073126 A1 | 3/2007 | Raridan |
| 2003/0073890 A1 | 4/2003 | Hanna | | 2007/0073128 A1 | 3/2007 | Hoarau et al. |
| 2003/0100840 A1 | 5/2003 | Sugiura et al. | | 2007/0078315 A1 | 4/2007 | Kling et al. |
| 2003/0156288 A1 | 8/2003 | Barnum et al. | | 2007/0078316 A1 | 4/2007 | Hoarau et al. |
| 2003/0181799 A1 * | 9/2003 | Lindekugel et al. ......... 600/344 | | 2007/0260129 A1 | 11/2007 | Chin |
| 2003/0187337 A1 | 10/2003 | Tarassenko et al. | | 2007/0260130 A1 | 11/2007 | Chin |
| 2003/0197679 A1 | 10/2003 | Ali et al. | | 2007/0260131 A1 | 11/2007 | Chin |
| 2003/0212316 A1 | 11/2003 | Leiden et al. | | 2007/0299328 A1 | 12/2007 | Chin et al. |
| 2003/0225323 A1 | 12/2003 | Kiani et al. | | 2008/0076987 A1 * | 3/2008 | Arizaga Ballesteros ...... 600/323 |
| 2004/0006261 A1 | 1/2004 | Swedlow et al. | | 2008/0081971 A1 * | 4/2008 | Ollerdessen ................ 600/323 |
| 2004/0024326 A1 | 2/2004 | Yeo et al. | | | | |
| 2004/0039272 A1 | 2/2004 | Abdul-Hafiz et al. | | FOREIGN PATENT DOCUMENTS | | |
| 2004/0039273 A1 | 2/2004 | Terry | | | | |
| 2004/0044276 A1 * | 3/2004 | Arnold ................ 600/323 | | DE | 3516338 | 11/1986 |
| 2004/0054291 A1 | 3/2004 | Schulz et al. | | DE | 37 03 458 | 8/1988 |
| 2004/0068164 A1 | 4/2004 | Diab et al. | | DE | 3938759 | 5/1991 |
| 2004/0092805 A1 | 5/2004 | Yarita | | DE | 4210102 | 9/1993 |
| 2004/0097797 A1 | 5/2004 | Porges et al. | | DE | 4423597 | 8/1995 |
| 2004/0098009 A1 | 5/2004 | Boecker et al. | | DE | 19632361 | 2/1997 |
| 2004/0117891 A1 | 6/2004 | Hannula et al. | | DE | 69123448 | 5/1997 |
| 2004/0143172 A1 * | 7/2004 | Fudge et al. ............... 600/344 | | DE | 19703220 | 7/1997 |
| 2004/0147824 A1 | 7/2004 | Diab et al. | | DE | 19640807 | 9/1997 |
| 2004/0158134 A1 | 8/2004 | Diab et al. | | DE | 19647877 | 4/1998 |
| 2004/0162472 A1 | 8/2004 | Berson et al. | | DE | 10030862 | 1/2002 |
| 2004/0167381 A1 | 8/2004 | Lichter et al. | | DE | 20318882 | 4/2004 |
| 2004/0186358 A1 | 9/2004 | Chernow et al. | | EP | 0127947 | 5/1984 |

| | | | | | |
|---|---|---|---|---|---|
| EP | 00194105 | 9/1986 | JP | 8256996 | 10/1996 |
| EP | 00204459 | 12/1986 | JP | 9192120 | 7/1997 |
| EP | 0 262 779 | 4/1988 | JP | 10216113 | 8/1998 |
| EP | 0315040 | 10/1988 | JP | 10216114 | 8/1998 |
| EP | 0314331 | 5/1989 | JP | 10216115 | 8/1998 |
| EP | 00352923 | 1/1990 | JP | 10337282 | 12/1998 |
| EP | 0 360 977 | 4/1990 | JP | 11019074 | 1/1999 |
| EP | 00430340 | 6/1991 | JP | 11155841 | 6/1999 |
| EP | 0435 500 | 7/1991 | JP | 11 188019 | 7/1999 |
| EP | 0572684 | 5/1992 | JP | 11244268 | 9/1999 |
| EP | 00497021 | 8/1992 | JP | 20107157 | 4/2000 |
| EP | 0529412 | 8/1992 | JP | 20237170 | 9/2000 |
| EP | 0531631 | 9/1992 | JP | 21245871 | 9/2001 |
| EP | 0566354 | 4/1993 | JP | 22224088 | 8/2002 |
| EP | 0587009 | 8/1993 | JP | 22282242 | 10/2002 |
| EP | 00630203 | 9/1993 | JP | 23153881 | 5/2003 |
| EP | 0 572 684 | 12/1993 | JP | 23153882 | 5/2003 |
| EP | 00615723 | 9/1994 | JP | 23169791 | 6/2003 |
| EP | 00702931 | 3/1996 | JP | 23194714 | 7/2003 |
| EP | 00724860 | 8/1996 | JP | 23210438 | 7/2003 |
| EP | 00793942 | 9/1997 | JP | 23275192 | 9/2003 |
| EP | 0 864 293 | 9/1998 | JP | 23339678 | 12/2003 |
| EP | 01006863 | 10/1998 | JP | 24008572 | 1/2004 |
| EP | 01006864 | 10/1998 | JP | 24089546 | 3/2004 |
| EP | 0875199 | 11/1998 | JP | 24113353 | 4/2004 |
| EP | 00998214 | 12/1998 | JP | 24135854 | 5/2004 |
| EP | 0 898 933 | 3/1999 | JP | 24148069 | 5/2004 |
| EP | 0898933 | 3/1999 | JP | 24148070 | 5/2004 |
| EP | 01332713 | 8/2003 | JP | 24159810 | 6/2004 |
| EP | 01469773 | 8/2003 | JP | 24166775 | 6/2004 |
| EP | 1502529 | 7/2004 | JP | 24194908 | 7/2004 |
| EP | 01491135 | 12/2004 | JP | 24202190 | 7/2004 |
| FR | 2685865 | 1/1992 | JP | 24248819 | 9/2004 |
| GB | 2 259 545 | 3/1993 | JP | 24248820 | 9/2004 |
| JP | 63275325 | 11/1988 | JP | 24261364 | 9/2004 |
| JP | 2013450 | 1/1990 | JP | 24290412 | 10/2004 |
| JP | 2111343 | 4/1990 | JP | 24290544 | 10/2004 |
| JP | 02 191434 | 7/1990 | JP | 24290545 | 10/2004 |
| JP | 2237544 | 9/1990 | JP | 24329406 | 11/2004 |
| JP | 03 173536 | 7/1991 | JP | 24329607 | 11/2004 |
| JP | 3170866 | 7/1991 | JP | 24329928 | 11/2004 |
| JP | 3245042 | 10/1991 | JP | 24337605 | 12/2004 |
| JP | 4174648 | 6/1992 | JP | 24344367 | 12/2004 |
| JP | 4191642 | 7/1992 | JP | 24351107 | 12/2004 |
| JP | 4332536 | 11/1992 | JP | 25034472 | 2/2005 |
| JP | 3124073 | 3/1993 | WO | WO 98/09566 | 10/1989 |
| JP | 5049624 | 3/1993 | WO | WO 90/01293 | 2/1990 |
| JP | 5049625 | 3/1993 | WO | WO 90/04352 | 5/1990 |
| JP | 3115374 | 4/1993 | WO | WO 91/01678 | 2/1991 |
| JP | 05 200031 | 8/1993 | WO | WO 91/11137 | 8/1991 |
| JP | 2005/200031 | 8/1993 | WO | WO 92/00513 | 1/1992 |
| JP | 5212016 | 8/1993 | WO | WO 92/21281 | 12/1992 |
| JP | 06 014906 | 1/1994 | WO | WO 93/09711 | 5/1993 |
| JP | 06014906 | 1/1994 | WO | WO 93/13706 | 7/1993 |
| JP | 6016774 | 3/1994 | WO | WO 93/16629 | 9/1993 |
| JP | 3116255 | 4/1994 | WO | WO 94/03102 | 2/1994 |
| JP | 6029504 | 4/1994 | WO | WO 94/23643 | 10/1994 |
| JP | 6098881 | 4/1994 | WO | WO 95/02358 | 1/1995 |
| JP | 06 154177 | 6/1994 | WO | WO 95/12349 | 5/1995 |
| JP | 6269430 | 9/1994 | WO | WO 95/16970 | 6/1995 |
| JP | 6285048 | 10/1994 | WO | WO 96/13208 | 5/1996 |
| JP | 7001273 | 1/1995 | WO | WO 96/39927 | 12/1996 |
| JP | 7124138 | 5/1995 | WO | WO 97/36536 | 10/1997 |
| JP | 7136150 | 5/1995 | WO | WO 97/36538 | 10/1997 |
| JP | 3116259 | 6/1995 | WO | WO 97/49330 | 12/1997 |
| JP | 3116260 | 6/1995 | WO | WO 98/17174 | 4/1998 |
| JP | 7155311 | 6/1995 | WO | WO 98/18382 | 5/1998 |
| JP | 7155313 | 6/1995 | WO | WO 98/43071 | 10/1998 |
| JP | 3238813 | 7/1995 | WO | WO 98/51212 | 11/1998 |
| JP | 7171139 | 7/1995 | WO | WO 98/57577 | 12/1998 |
| JP | 3134144 | 9/1995 | WO | WO 99/00053 | 1/1999 |
| JP | 7236625 | 9/1995 | WO | WO 99/32030 | 7/1999 |
| JP | 7246191 | 9/1995 | WO | WO 99/47039 | 9/1999 |

| | | |
|---|---|---|
| WO | WO 99/63884 | 12/1999 |
| WO | WO 00/21438 | 4/2000 |
| WO | WO 00/28888 | 5/2000 |
| WO | WO 00/59374 | 10/2000 |
| WO | WO 01/13790 | 3/2001 |
| WO | WO 01/16577 | 3/2001 |
| WO | WO 01/17421 | 3/2001 |
| WO | WO 01/47426 | 3/2001 |
| WO | WO 01/40776 | 6/2001 |
| WO | WO 01/67946 | 9/2001 |
| WO | WO 01/76461 | 10/2001 |
| WO | WO 02/14793 | 2/2002 |
| WO | WO 02/35999 | 5/2002 |
| WO | WO 02/062213 | 8/2002 |
| WO | WO 02/074162 | 9/2002 |
| WO | WO 02/085202 | 10/2002 |
| WO | WO 03/000125 | 1/2003 |
| WO | WO 03/001180 | 1/2003 |
| WO | WO 03/009750 | 2/2003 |
| WO | WO 03/011127 | 2/2003 |
| WO | WO 03/020129 | 3/2003 |
| WO | WO 03/039326 | 5/2003 |
| WO | WO 03/063697 | 8/2003 |
| WO | WO 03/073924 | 9/2003 |
| WO | WO 2004/000114 | 12/2003 |
| WO | WO 2004/006748 | 1/2004 |
| WO | WO 2004/069046 | 8/2004 |
| WO | WO 2004/075746 | 9/2004 |
| WO | WO 2005/002434 | 1/2005 |
| WO | WO 2005/009221 | 2/2005 |
| WO | WO 2005/010567 | 2/2005 |
| WO | WO 2005/010568 | 2/2005 |
| WO | WO 2005/020120 | 3/2005 |
| WO | WO 2005/065540 | 7/2005 |
| WO | WO 2006/104790 | 10/2006 |

OTHER PUBLICATIONS

U.S. Appl. No. 11/252,396, filed Sep. 22, 2006, Hoarau.
U.S. Appl. No. 11/252,635, filed Sep. 22, 2006, Hoarau.
U.S. Appl. No. 11/252,636, filed Sep. 22, 2006, Hoarau.
U.S. Appl. No. 11/252,696, filed Sep. 22, 2006, Hoarau.
U.S. Appl. No. 11/252,704, filed Sep. 22, 2006, Hoarau.
U.S. Appl. No. 11/527,762, filed Sep. 26, 2006, Ollerdessen.
U.S. Appl. No. 12/004,816, filed Dec. 21, 2007, Bowman et al.
U.S. Appl. No. 12/005,023, filed Dec. 21, 2007, Bowman et al.
Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1990).
Zahar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).
Aoyagi, T., et al.; "Analysis of Motion Artifacts in Pulse Oximetry," *Japanese Society ME*, vol. 42, p. 20 (1993) (Article in Japanese—contains English summary of article).
Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).
Vincente, L.M., et al.; "Adaptive Pre-Processing of Photoplethysmographic Blood Volume Pulse Measurements," pp. 114-117 (1996).
Plummer, John L., et al.; "Identification of Movement Artifact by the Nellcor N-200 and N-3000 Pulse Oximeters," *Journal of clinical Monitoring*, vol. 13, pp. 109-113 (1997).
Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).
Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30th-Nov. 2nd, 1997; pp. 2326-2329.
Block, Frank E., Jr., et al.; "Technology evaluation report: Obtaining pulse oximeter signals when the usual probe cannot be used," *International journal of clinical Monitoring and Computing*, vol. 14, pp. 23-28 (1997).
Nijland, Roel, et al.; "Validation of Reflectance Pulse Oximetry: An Evaluation of a new Sensor in Piglets," *Journal of Clinical Monitoring*, vol. 13, pp. 43-49 (1997).
Soto, Denise A.; "A Comparative Study of Pulse Oximeter Measurements: Digit Versus Earlobe," Master of Science Thesis, California State University Dominguez Hills, May 1997, 46 pgs.
Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).
Izumi, Akio, et al.; "Accuracy and Utility of a New Reflectance Pulse Oximeter for Fetal Monitoring During Labor," *Journal of Clinical Monitoring*, vol. 13, pp. 103-108 (1997).
Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).
"Smaller Product, Tighter Tolerances Pose Dispensing Challenges for Medical Device Manufacturer," *Adhesives Age*, pp. 40-41 (Oct. 1997).
Buschman, J.P., et al.; "Principles and Problems of Calibration of Fetal Oximeters," *Biomedizinische Technik*, vol. 42, pp. 265-266 (1997).
Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.
Leahy, Martin J., et al.; "Sensor Validation in Biomedical Applications," *IFAC Modelling and Control in Biomedical Systems*, Warwick, UK; pp. 221-226 (1997).
Barreto, Armando B., et al.; "Adaptive LMS Delay Measurement in dual Blood Volume Pulse Signals for Non-Invasive Monitoring," *IEEE*, pp. 117-120 (1997).
Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.
DeKock, Marc; "Pulse Oximetry Probe Adhesive Disks: a Potential for Infant Aspiration," *Anesthesiology*, vol. 89, pp. 1603-1604 (1998).
East, Christine E., et al.; "Fetal Oxygen Saturation and Uterine Contractions During Labor," *American Journal of Perinatology*, vol. 15, No. 6, pp. 345-349 (Jun. 1998).
Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1909 (Oct. 1998).
Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.
König, Volker, et al.; "Reflectance Pulse Oximetry—Principles and Obstetric Application in the Zurich System," *Journal of Clinical Monitoring and Computing*, vol. 14, pp. 403-412 (1998).
Nogawa, Masamichi, et al.; "A Novel Hybrid Reflectance Pulse Oximater Sensor with improved Linearity and General Applicability to Various Portions of the Body," *Proceedings of the 20th Annual International Conference of the IEEE Engineering in Medicine and Biology Society*, vol. 20, No. 4, pp. 1858-1861 (1998).
Hayes, Matthew J., et al.; "Quantitative evaluation of photoplethysmographic artifact reduction for pulse oximetry," *SPIE*, vol. 3570, pp. 138-147 (Sep. 1998).
Edrich, Thomas, et al.; "Can the Blood Content of the Tissues be Determined Optically During Pulse Oximetry Without Knowledge of the Oxygen Saturation?—An In-Vitro Investigation," *Proceedings of* the 20th Annual International conference of the IEEE Engineering in Medicine and Biology Society, vol. 20, No. 6, pp. 3072-3075 (1998).

Hayes, Matthew J., et al.; "Artifact reduction in photoplethysmography," Applied Optics, vol. 37, No. 31, pp. 7437-7446 (Nov. 1998).

Such, Hans Olaf; "Optoelectronic Non-invasive Vascular Diagnostics Using multiple Wavelength and Imaging Approach," Dissertation, (1998).

Lutter, N., et al.; "Comparison of Different Evaluation Methods for a Multi-wavelength Pulse Oximeter," Biomedizinische Technik, vol. 43, (1998).

Ferrell, T.L., et al.; "Medical Telesensors," SPIE, vol. 3253, pp. 193-198 (1998).

Todd, Bryan, et al.; "The Identification of Peaks in Physiological Signals," Computers and Biomedical Research, vol. 32, pp. 322-335 (1999).

Rhee, Sokwoo, et al.; "Design of a Artifact-Free Wearable Plethysmographic Sensor," Proceedings of the First joint BMES/EMBS Conference, Oct. 13-16, 1999, Altanta, Georgia, p. 786.

Rohling, Roman, et al.; "Clinical Investigation of a New Combined Pulse Oximetry and Carbon Dioxide Tension Sensor in Adult Anaesthesia," Journal o Clinical Monitoring and Computing, vol. 15; pp. 23-27 (1999).

Ikeda, Kenji, et al.; "Improvement of Photo-Electric Plethysmograph Applying Newly Developed Opto-Electronic Devices," IEEE Tencon, pp. 1109-1112 (1999).

Kaestle, S.; "An Algorithm for Reliable Processing of Pulse Oximetry Signals Under strong Noise Conditions," Dissertation Book, Lubeck University, Germany (1999).

Seelbach-Göbel, Birgit, et al.; "The prediction of fetal acidosis by means of intrapartum fetal pulse oximetry," Am J. Obstet. Gynecol., vol. 180, No. 1, Part 1, pp. 73-81 (1999).

Yang, Boo-Ho, et al.; "Development of the ring sensor for healthcare automation," Robotics and Autonomous Systems, vol. 30, pp. 273-281 (2000).

Rhee, Sokwoo, et al.; "Artifact-Resistant, Power-Efficient Design of Finger-Ring Plethysmographic Sensor—Part I: Design and Analysis," Proceedings of the 22nd Annual EMBS International Conference, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," Proceedings of the 22nd Annual EMBS International Conference, Chicago, Illinois; Jul. 23-28, 2000; pp. 2796-2799.

Vicenzi, Martin N.; "Transesophageal versus surface pulse oximetry in intensive care unit patients," Crit. Care Med.; vol. 28, No. 7, pp. 2268-2270 (2000).

Goldman, Julian M.; "Masimo Signal Extraction Pulse Oximetry," Journal of Clinical Monitoring and Computing, vol. 16, pp. 475-483 (2000).

Coetzee, Frans M.; "Noise-Resistant Pulse Oximetry Using a Synthetic Reference Signal," IEEE Transactions on Biomedical Engineering, vol. 47, No. 8, Aug. 2000, pp. 1018-1026.

Nilsson, Lena, et al.; "Monitoring of Respiratory Rate in Postoperative Care Using a New Photoplethysmographic Technique," Journal of Clinical Monitoring and Computing, vol. 16, pp. 309-315 (2000).

Nijiand, Mark J.M., et al.; "Assessment of fetal scalp oxygen saturation determination in the sheep by transmission pulse oximetry," Am. J. Obstet Gynecol., vol. 183, No. 6, pp. 1549-1553 (Dec. 2000).

Edrich, Thomas, et al.; "Pulse Oximetry: An Improved In Vitro Model that Reduces Blood Flow-Related Artifacts," IEEE Transactions on Biomedical Engineering, vol. 47, No. 3, pp. 338-343 (Mar. 2000).

Schulz, Christian Eric; "Design of a Pulse Oximetry Sensor Housing Assembly," California State University Master's Thesis, UMI Dissertation Services, UMI No. 1401306, (May 2000) 63 pages.

Yao, Jianchu, et al.; "Design of a Plug-and-Play Pulse Oximeter," Proceedings of the Second Joint EMBS/BMES Conference, Houston, Texas, Oct. 23-26, 2002; pp. 1752-1753.

Aoyagi, T., et al.; "Pulse Oximeters: background, present and future," Neonatal Care, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," Journal of the Japanese Society of Emergency Medicine, Kanto Region, vol. 21, pp. 26-27 (2000) (Article in Japanese—contains English summary of article).

Kaestle, S.; "Determining Artefact Sensitivity of New Pulse Oximeters in Laboratory Using Signals Obtained from Patient," Biomedizinische Technik, vol. 45 (2000).

Cubeddu, Rinaldo, et al.; "Portable 8-channel time-resolved optical imager for functional studies of biological tissues," Photon Migration, Optical Coherence Tomography, and Microscopy, Proceedings of SPIE, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," Sensor and Actuators, vol. B-76, pp. 527-530 (2001).

Cysewska-Sobusaik, Anna; "Metrological Problems With noninvasive Transillumination of Living Tissues," Proceedings of SPIE, vol. 4515, pp. 15-24 (2001).

Rhee, Sokwoo, et al.; "Artifact-Resistant, Power-Efficient Design of Finger-Ring Plethysmographic Sensor," IEEE Transactions on Biomedical Engineering, vol. 48, No. 7, pp. 795-805 (Jul. 2001).

Belal, Suliman Yousef, et al.; "A fuzzy system for detecting distorted plethysmogram pulses in neonates and paediatric patients," Physiol. Meas., vol. 22, pp. 397-412 (2001).

Hayes, Matthew J., et al.; "A New Method for Pulse Oximetry Possessing Inherent Insensitivity to Artifact," IEEE Transactions on Biomedical Engineering, vol. 48, No. 4, pp. 452-461 (Apr. 2001).

Gosney, S., et al.; "An alternative position for the pulse oximeter probe," Anaesthesia, vol. 56, p. 493 (2001).

Silva, Sonnia Maria Lopez, et al.; "NIR transmittance pulse oximetry system with laser diodes," Clinical Diagnostic Systems, Proceedings of SPIE, vol. 4255, pp. 80-87 (2001).

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Earthrowl-Gould, T., et al.; "Chest and abdominal surface motion measurement for continuous monitoring of respiratory function," Proc. Instn Mech Engrs, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," Respiratory Care, Vo. 47, No. 1, pp. 48-60 (Jan. 2002).

Jopling, Michae W., et al.; "Issues in the Laboratory Evaluation of Pulse Oximeter Performance," Anesth Analg, vol. 94, pp. S62-S68 (2002).

Gostt, R., et al.; "Pulse Oximetry Artifact Recognition Algorithm for Computerized Anaesthetic Records," Journal of Clinical Monitoring and Computing Abstracts, p. 471 (2002).

Chan, K.W., et al.; "17.3: Adaptive Reduction of Motion Artifact from Photoplethysmographic Recordings using a Variable Step-Size LMS Filter," IEEE, pp. 1343-1346 (2002).

Relente, A.R., et al.; "Characterization and Adaptive Filtering of Motion Artifacts in Pulse Oximetry using Accelerometers," Proceedings of the Second joint EMBS/BMES Conference, Houston, Texas, Oct. 23-26, 2002; pp. 1769-1770.

Yamaya, Yoshiki, et al.; "Validity of pulse oximetry during maximal exercise in normoxia, hypoxia, and hyperoxia," J. Appl. Physiol., vol. 92, pp. 162-168 (2002).

Lutter, Norbert O., et al.; "False Alarm Rates of Three Third-Generation Pulse Oximeters in PACU, ICU and IABP Patients," Anesth Analg, vol. 94, pp. S69-S75 (2002).

Lutter, N., et al.; "Accuracy of Noninvasive Continuous Blood Pressure; Measurement Utilising the Pulse Transit Time," Journal of clinical Monitoring and Computing, vol. 17, Nos. 7-8, pp. 469 (2002).

Liu, Ying, et al.; "Sensor design of new type reflectance pulse oximetry," Optics in Health Care and Biomedical Optics: Diagnostics and Treatment, Proceedings of SPIE, vol. 4916, pp. 98-102 (2002).

Kyriacou, Panayiotis A., et al.; "Esophageal Pulse Oximetry Utilizing Reflectance Photoplethysmography," IEEE Transactions on Biomedical Engineering, vol. 49, No. 11, pp. 1360-1368 (Nov. 2002).

Kyriacou, P. A., et al.; "Investigation of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M.N., et al.; "In vivo application of a minimally invasive oximetry based perfusion sensor," *Proceedings of the Second Joint EMBS/BMES Conference*, Houston, Texas; Oct. 23-26, 2002; pp. 1789-1790.

Yoon, Gilwon, et al.; Multiple diagnosis based on Photoplethysmography: hematocrib, SpO2, pulse and respiration, *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Pothisam, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25$^{th}$ Annual International Conference of the IEEE EMBS*, Cancun, Mexico, Sep. 17-21, 2003; pp. 2439-2442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Mendelson, Y., et al.; "Measurement Site and Photodetector Size Considerations in Optimizing Power Consumption of a Wearable Reflectance Pulse Oximeter," *Proceedings of the 25$^{th}$ Annual International conference of the IEEE EMBS*, Cancun, Mexico, Sep. 17-21, 2003; pp. 3016-3019.

Itoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and SpO2 using a Miniature earlobe sensor," *Jinko Kokyo (Aritificial Respiration)*, vol. 20, No. 1, pp. 24-29 (2003).

Lebak, J.W., et al.; "Implementation of a Standards-Based Pulse Oximeter on a Wearable, Embedded Platform," *Proceeding of the 25$^{th}$ Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceeding of the 25$^{th}$ Annual International Conference of the IEEE EMBS*, Cancun, Mexico, Sep. 17-21, 2003; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25$^{th}$ Annual International Conference of the IEEE EMBS*, Cancun, Mexico; Sep. 17-21, 2003; pp. 1394-1397.

Pujary, C., et al.; "Photodetector Size Considerations in the Design of a Noninvasive Reflectance Pulse Oximeter for Telemedicine Applications," *IEEE*, pp. 148-149 (2003).

A. Johansson; "Neural network for photoplethysmographic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," *Proceedings o the 26$^{th}$ Annual International conference of the IEEE EMBS*, San Francisco, California, Sep. 1-5, 2004, pp. 4759-4762.

Kocher, Serge, et al.; "Performance of a Digital $PCO_2/SPO_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26$^{th}$ Annual International conference of the IEEE EMBS*, San Francisco, California, Sep. 1-5, 2004; pp. 2153-2156.

Nuhr, M., et al.: "Forehead $SpO_2$ monitoring compared to finger $SpO_2$ recording in emergency transport," *Anaesthesia*, vol. 59, pp. 390-393 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Kocher, Serge, et al.; "Performance of a Digital $PCO_2/SPO_2$ Ear Sensor," *Journal of Clinical Monitoring and Computing*, vol. 18, pp. 75-79 (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul. 2004); (Article in Japanese—contains English summary of article).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the 26$^{th}$ Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

\* cited by examiner

MULTIPLE CONFIGURATION MEDICAL SENSOR AND TECHNIQUE FOR USING THE SAME

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Two categories of pulse oximetry sensors in common use may be classified by their pattern of use: the disposable and the reusable sensor. Disposable sensors are typically flexible bandage-type structures that may be attached to the patient with adhesive materials, providing a contact between the patient's skin and the sensor components.

Occasionally, healthcare workers may inadvertently use a flexible, disposable sensor indicated for one tissue site on a tissue site for which the sensor is not designed. For example, a sensor designed to fold around the tip of a digit may be mistakenly placed flat on the forehead of a patient. A digit sensor may be arranged in a transmission-type configuration, with the sensing elements designed to lie on opposing sides of the tissue. Laying such a sensor flat against the skin on the forehead in a reflectance-type configuration, with the sensing elements side-by-side, may contribute to measurement inaccuracies. The sensing elements may have been calibrated for transmission-type use, and may not operate correctly when applied in a reflectance-type configuration.

Sensor misplacement may also contribute to a poor fit of the sensor against the tissue, as a digit sensor may be too large or heavy to be supported by its adhesive on the forehead, and thus may be easily dislodged by patient movement. Further, the relatively large surface area of a digit sensor may not conform to the curved surface of the forehead, and thus may be susceptible to signal artifacts associated with movement of the sensor relative to the tissue. Additionally, signal artifacts may be associated with a poor fit of the sensor against a patient's tissue. An ill-fitting sensor may allow ambient light to reach the detecting elements of the sensor, which may also interfere with the amount of light detected. An ill-fitting sensor may also be more susceptible to mechanical deformation than a sensor that is tightly adhered to the skin.

SUMMARY

Certain aspects commensurate in scope with the originally claimed invention are set forth below. It should be understood that these aspects are presented merely to provide the reader with a brief summary of certain forms that the invention might take and that these aspects are not intended to limit the scope of the invention. Indeed, the invention may encompass a variety of aspects that may not be set forth below.

There is provided a sensor that includes a conformable sensor body having a first configuration adapted to be applied to a first tissue site and a second configuration adapted to be applied to a second tissue site; and an emitter and a detector disposed on the sensor body.

There is also provided a sensor that includes a sensor body having a first portion and a second portion that is removable from the first portion, wherein the first portion of the sensor body is adapted to be applied to a patient's forehead and the first portion and the second portion of the sensor body are adapted to be applied to a patient's digit; and an emitter and a detector disposed on the sensor body.

There is also provided a sensor that includes a conformable sensor body having a first configuration adapted to be applied to a first tissue site and a second configuration adapted to be applied to a second tissue site, the first configuration being adapted to measure a first physiological parameter and the second configuration being adapted to be measure a second physiological parameter; and an emitter and a detector disposed on the sensor body.

There is also provided a pulse oximetry system that includes a pulse oximetry monitor; and a sensor adapted to be operatively coupled to the monitor. The sensor includes a conformable sensor body having a first configuration adapted to be applied to a first tissue site and a second configuration adapted to be applied to a second tissue site; and an emitter and a detector disposed on the sensor body.

There is also provided a method of operating a multi-configuration sensor that includes emitting light into a patient's tissue with an emitter disposed on a sensor body; detecting the light with a detector disposed on the sensor body; and providing a signal related to whether the sensor body is in a first configuration or a second configuration.

There is also provided a method of manufacturing a sensor that includes providing a conformable sensor body having a first configuration adapted to be applied to a first tissue site and a second configuration adapted to be applied to a second tissue site; and providing an emitter and a detector disposed on the sensor body.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In accordance with the present technique, sensors for pulse oximetry or other applications utilizing spectrophotometry are provided that may be used in multiple configurations and/or at multiple patient tissue sites. Such sensors may provide distinct advantages for healthcare practitioners. For example, as such sensors may be appropriate for use on a patient digit or a patient forehead, a healthcare practitioner may move a digit sensor to the forehead without using a new sensor, which may cut down on sensor waste and thus may reduce costs. Further, such flexibility may allow an emergency monitor to be stocked with fewer sensors, as the available sensors may be configured to be used on multiple patient tissue sites, as appropriate. Additionally, multiple configuration sensors may change configuration to allow a closer fit to multiple tissue sites, preventing signal artifacts associated with a poor sensor fit to the tissue.

Figure 1:
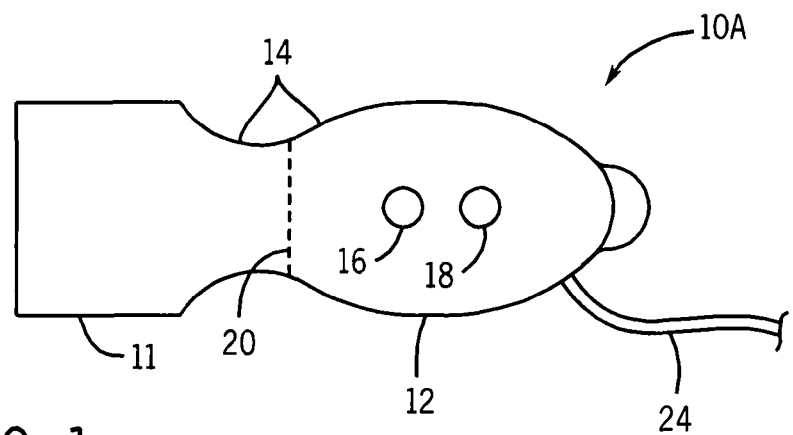
FIG. 1 illustrates a perspective view of multiple configuration medical sensor according to the present techniques.

Sensors are disclosed herein having multiple possible configurations. FIG. 1 illustrates an exemplary bandage-type sensor 10A appropriate for use on a patient's digit (see FIG. 2) or a patient's forehead (see FIG. 4). The sensor body 14 includes an emitter 16 and a detector 18 disposed on its surface. As depicted, the emitter 16 and detector 18 may be arranged in a reflectance-type configuration in which the emitter 16 and detector 18 that are typically placed on the same side of the sensor site. Reflectance type sensors may operate by emitting light into the tissue and detecting the light that is transmitted and scattered by the tissue. Reflectance type sensors detect light photons that are scattered back to the detector 18.

Figure 2:
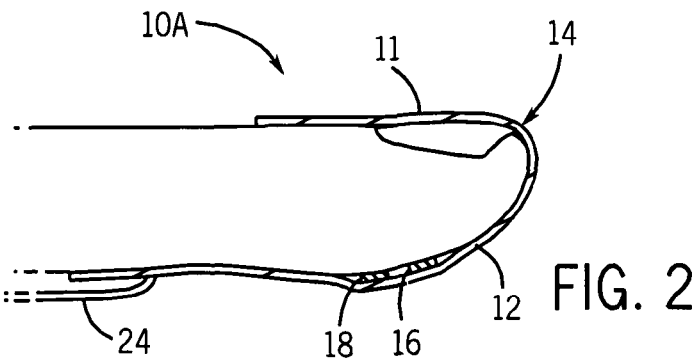
FIG. 2 is cross-sectional view of the medical sensor of FIG. 1 applied to a patient's digit.

The sensor body 14 may include a detecting portion 12 that includes the emitter 16 and the detector 18 and any electrical connectors, such as wire leads, that may operatively connect the emitter 16 and the detector 18 to a cable 24, which may be connected to a downstream monitoring device. The sensor body 14 may also include a removable portion 11 that may be separated from the detecting portion 12 by a perforation 20. As shown in FIG. 2, the detecting portion 12 and the removable portion 11 of the sensor body 14 may be wrapped around a patient's digit to achieve a substantially conforming and secure fit. The removable portion 11 provides additional surface area that allows the sensor body 14 to be able to wrap around the digit, which may provide a more secure fit for the sensor 10A. The sensor 10A may also include an adhesive layer (not shown) in order to enhance the sensor's fit to the tissue. As shown, the emitter 16 and the detector 18 may be arranged to be secured to the palmar side of the digit. Alternatively, the sensor 10A may be applied to the digit such that the emitter 16 and the detector 18 are secured to the nail side of the digit.

Figure 3:
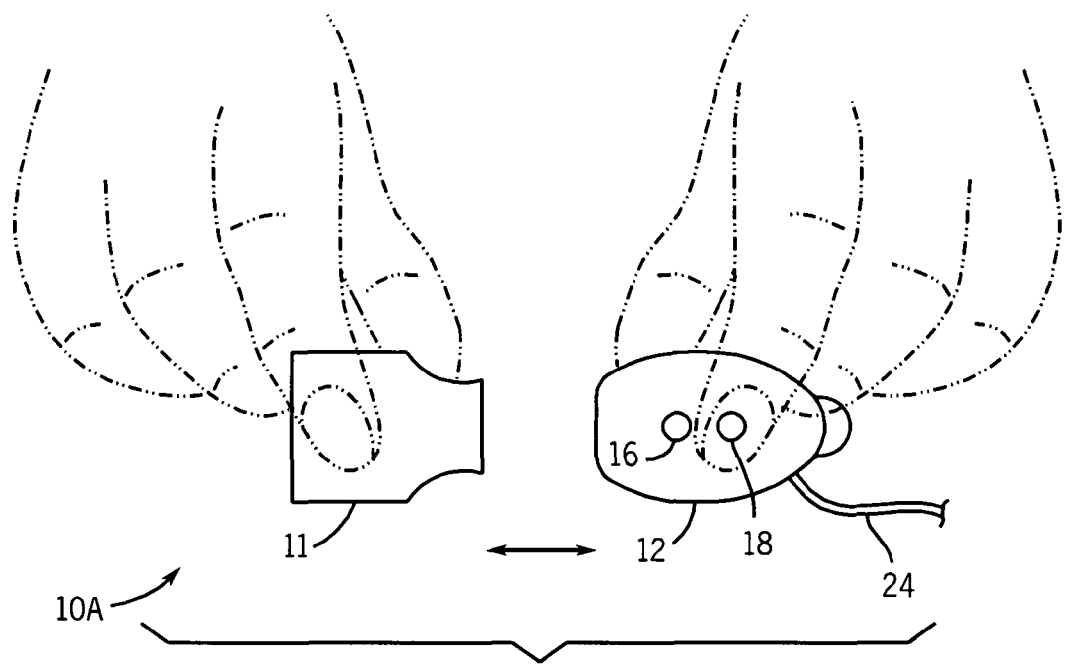
FIG. 3 illustrates portions of medical sensor of FIG. 1 being separated to switch to a different configuration.
Figure 4:
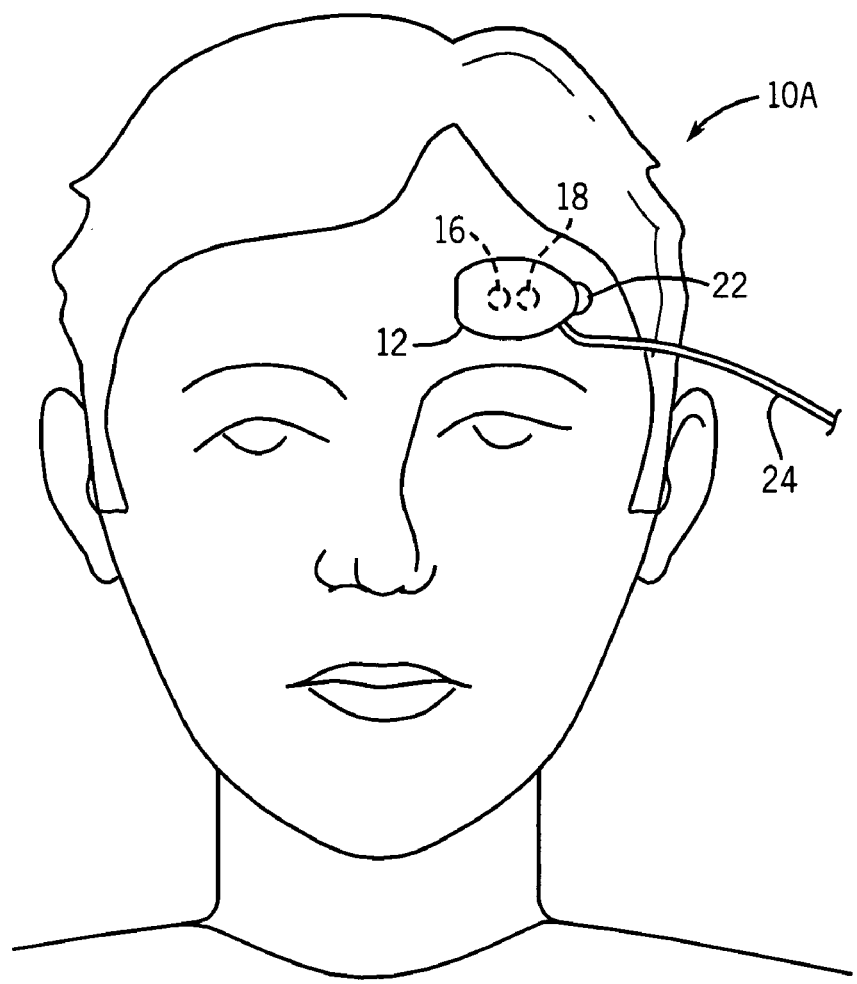
FIG. 4 shows an alternate configuration of the medical sensor of FIG. 1 applied to a patient's forehead after a portion of the sensor has been removed.

Illustrated in FIG. 3 is the sensor 10A with the removable portion 11 removed from the detecting portion 12. As shown, the detecting portion 12 retains the ability to measure a physiological parameter because the emitter 16, the detector 18, and the cable 24 are all included in the detecting portion 12 while being configured to have a smaller surface area that may be more appropriate for use on a different tissue site, such as a forehead, an ear, or a foot. In certain embodiments, the detecting portion 12 may be removed from the removable portion 11 through tearing along the perforation line 20. In other embodiments, the removable portion 11 may be cut away from the detecting portion 12. After removal of the removable portion 11, the detecting portion of the sensor 10A may be placed on a patient's forehead, as shown in FIG. 4.

The detecting portion 12 may also include a flap 22 that may assist in the placement and/or removal of the detecting portion 12 from the patient's forehead.

In certain embodiments, a user may input information about the configuration of the sensor 10A into a downstream medical device, such as a pulse oximetry monitor. For example, a user may input that the sensor 10A is in a digit or a forehead configuration so that a monitor may process the sensor signals appropriately. Alternatively, a reflectance sensor's emitter 16 and detector 18 may be calibrated to provide substantially accurate readings on both a digit and a forehead without any change in signal processing that is dependent on sensor configuration.

Figure 5A:
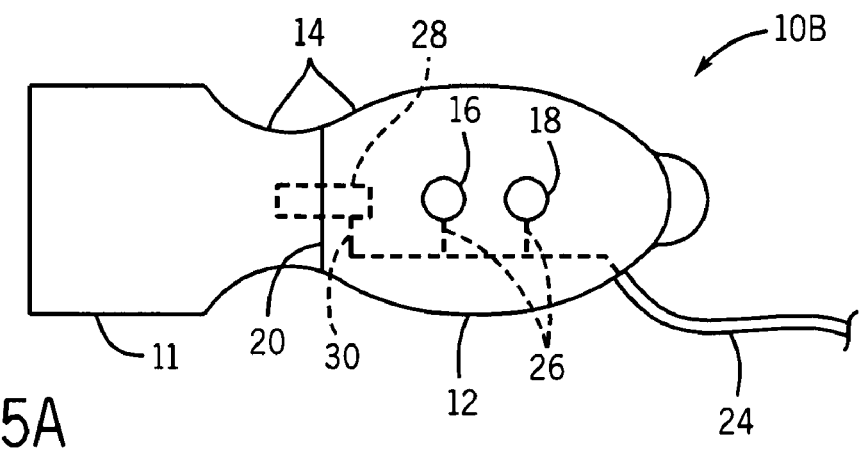
FIG. 5A is an alternate embodiment of a multiple configuration medical sensor including a breakable circuit.
Figure 5B:
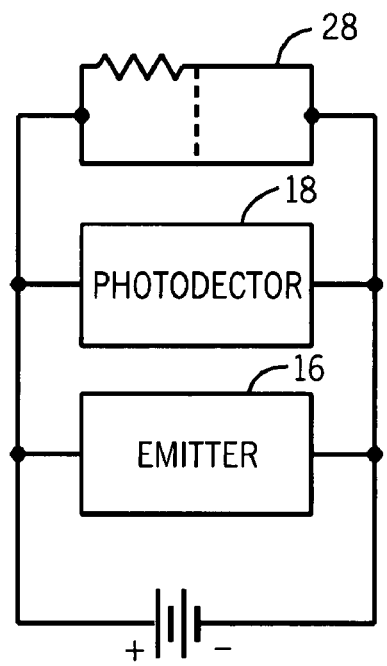
FIG. 5B is a schematic view of the breakable circuit of the sensor of FIG. 5A.

Sensors are also provided that may provide an indicator, such as an electrical signal, to a downstream medical device that may indicate in which position or configuration a sensor has been applied to a patient. FIG. 5A illustrates a sensor 10B that includes an indicator circuit 28 that is closed when the removable portion 11 is still attached to the detecting portion 12. The indicator circuit 28 may be disposed on the sensor body 14 such that a portion of the circuit 28 is on the removable portion 11 and a portion of the circuit 28 is on the detecting portion 12. The detecting portion 12 may also include the emitter 16, the detector 18, wire leads 26 adapted to carry signals to and from the emitter 16 and the detector 18, and a cable 24. When the removable portion 11 is separated from the detecting portion, the circuit opens (see FIG. 6). The indicating circuit wire lead 30 may send an electrical signal through the cable 24 to a downstream monitor, which may associate an open circuit signal with a forehead sensor configuration and a closed circuit signal with a digit sensor configuration. As illustrated in FIG. 5B, the indicator circuit 28 may be arranged in parallel with the circuitry for the emitter 16 and the detector 18 so that the removal of the removable portion 11 and the resultant open circuit may not affect the sensing ability of the emitter 16 and detector 18.

Figure 6:
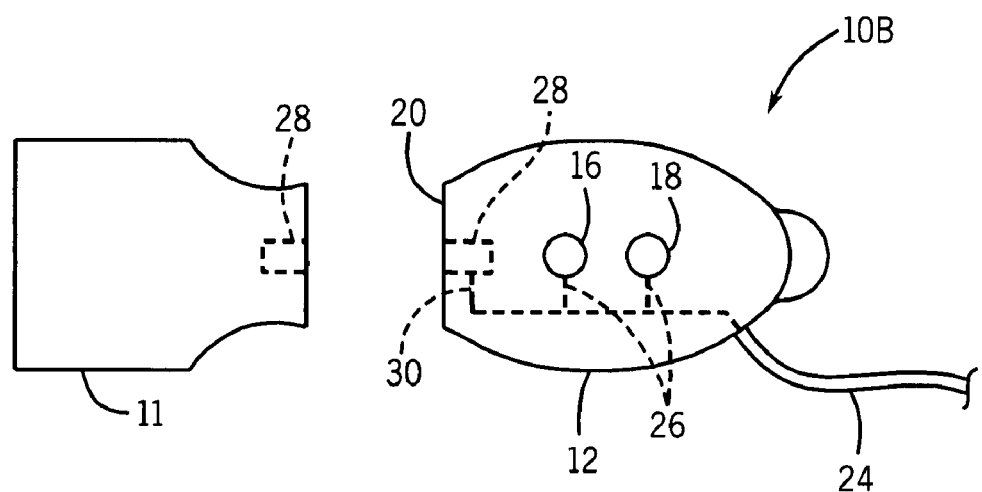
FIG. 6 shows an alternative configuration of the sensor of FIG. 5A in which the circuit is open after a portion of the sensor has been removed.

As shown in FIG. 6, when the removable portion 11 is detached from the detecting portion 12, the indicator circuit 28 is broken. Generally, it is envisioned that the portion of the indicator circuit along the separation line 20 be a conductive material that is either easily broken by hand or is easily cut by scissors. For example, the indicator circuit 28 may include thin foil material or a thin semiconductive ceramic in the portion of the circuit 28 that connects the removable portion 11 from the detecting portion 12.

Figure 7:
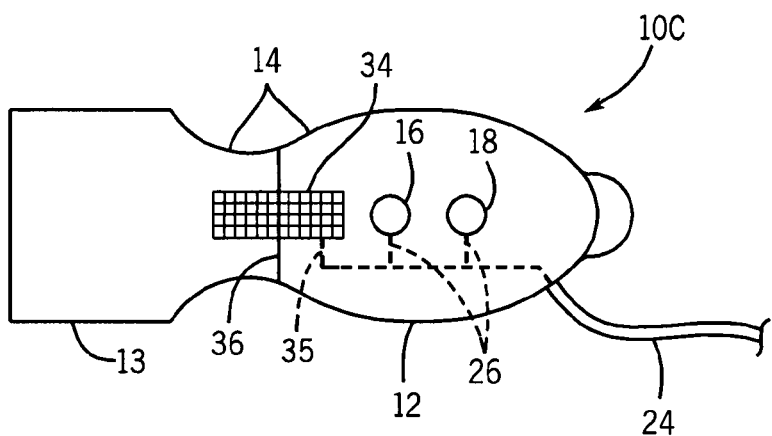
FIG. 7 illustrates an exemplary multiple configuration medical sensor including a pressure sensor.
Figure 8:
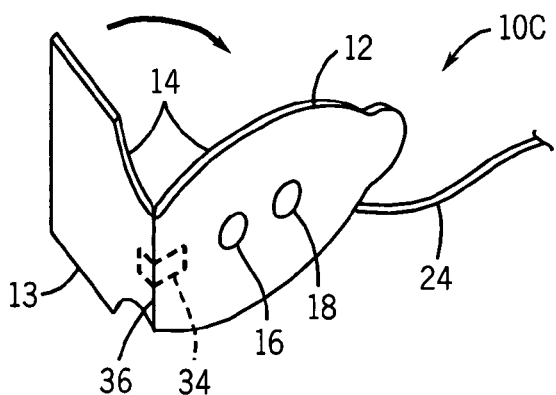
FIG. 8 is a view of the sensor of FIG. 7 with a portion of the sensor folded back.

In one embodiment, a sensor may be configured such that the transition between a first configuration and a second configuration may be achieved through bending or folding the sensor body rather than removing a portion of the sensor body. For example, FIG. 7 illustrates an exemplary sensor 10C that includes a pressure sensor 34 disposed on a fold line 36, which may be indicated by a printed line 36 on the sensor body 14. The pressure sensor 34 may be adapted to provide an electrical signal through a wire lead 35 that may be routed through a cable 24, along with any other wire leads, such as leads 26 that may provide electrical signals to and from an emitter 16 and detector 18 pair. For example, the electrical signal may be indicative of a force that may be associated with the typical pressure of a digit pressing against the tissue-contacting surface of the sensor body 14. The sensor 10C may be switched from the digit configuration to the forehead configuration by folding the foldable portion 13 back against the detecting portion 12. Shown in FIG. 8 is the sensor 10C in a folded position, with foldable portion 13 folded back against the exterior, non-tissue-contacting surface of portion 12. In certain embodiments, the exterior surface of either foldable portion 13 and/or detecting portion 12 may include adhesives, snaps, slots, or other securing devices to hold the foldable portion 13 relatively flat against the detecting portion 12. While in the folded position, the pressure sensor 34 may send a signal to a downstream monitor that is characteristic of the folded configuration, which may be associated with forehead placement of the sensor 10C.

In certain embodiments, the pressure sensor 34 may be disposed on the sensor body as electrodes, such as silver electrodes, printed as a matrix of intersecting rows and columns. An additional layer of semiconductive ink may provide an electrical resistance at each intersection on the matrix. Sandwiching these two layers together may create an array sensor. When a force is applied, the change in resistance is measured. Changing the formulation of the ink may produce different sensitivity ranges. Additionally, varying the spacing between rows and columns may yield finer resolution. In certain embodiments, a force-sensitive structure may have a spatial resolution, or sensor electrode spacing, of at least $0.0229 \text{ mm}^2$. An example of a resistance sensor that is appropriate for use with a sensor 10 according to the present techniques is Flexiforce® film or flexible circuits, available from Tekscan (South Boston, Mass.). Pressure measurements may also be made by strain-gauge sensors or potentiometers that detect bending, such as those available from Flexpoint Sensor Systems, Inc. (Draper, Utah). Additionally, the pressure sensor 34 may include polymers that are force-sensitive resistor materials. Force-sensitive resistor materials, such as those available from Interlink (Carptenteria, Calif.) and Advanced Composites Technology (Boston, Mass.) have a resistance variation under load. A force sensing resistor may be a piezoresistivity conductive polymer, which changes resistance in a predictable manner following application of force to its surface that may be a polymer sheet that has had the sensing film applied by screen printing. The sensing film typically includes both electrically conducting and non-conducting particles suspended in matrix. The particle sizes may be of the order of fraction of microns, and the particles may be formulated to reduce the temperature dependence, improve mechanical properties and increase surface durability. Applying a force to the surface of the sensing film causes particles to touch the conducting electrodes, changing the resistance of the film. Such a polymer-based force-sensitive resistor may be advantageous as it utilizes a relatively simple interface and can operate satisfactorily in moderately hostile environments. In certain embodiments, the pressure sensor 34 may take the form of a capacitance sensor. In such sensors, the capacitance is inversely proportional to the distance between the electrodes of the sensor. An exemplary capacitance-based sensor, TactArray, is available from Pressure Profile Systems (Los Angeles, Calif.). In certain embodiments, the capacitance sensor may be sensitive to forces or pressures from 1 psi to 200 psi.

A multiple configuration sensor may also be adapted to measure in reflectance mode in one configuration and in transmission mode in another configuration. While reflectance-type sensors include an emitter 16 and a detector 18 that lie side-by-side, transmission type sensors include an emitter 16 and detector 18 that are typically placed on opposing sides of the sensor site. If the sensor site is a fingertip, for example, the sensor is positioned over the patient's fingertip such that the emitter 16 and detector 18 lie on either side of the patient's nail bed. In other words, the sensor 10 is positioned so that the emitter 16 is located on the patient's fingernail and the detector 18 is located 180° opposite the emitter 16 on the patient's finger pad. During operation, the emitter 16 shines one or more wavelengths of light through the patient's fingertip and the light received by the detector 18 is processed to determine various physiological characteristics of the patient. In each of the embodiments discussed herein, for either reflectance-type or transmission-type sensors, it should be understood that the locations of the emitter 16 and the detector 18 may be exchanged. For example, the detector 18 may be located at the top of the finger and the emitter 16 may be located underneath the finger. In either arrangement, the sensor will perform in substantially the same manner. A sensor may also be a "transflectance" sensor, such as a sensor that may subtend a curved tissue surface, such as portion of a baby's heel.

Figure 9:
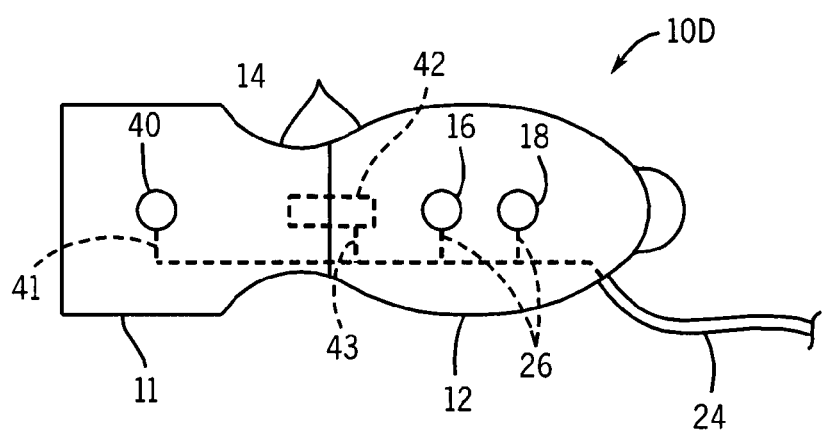
FIG. 9 illustrates an exemplary transmission/reflectance medical sensor including a sensing element disposed on a removable part of the sensor.
Figure 10:
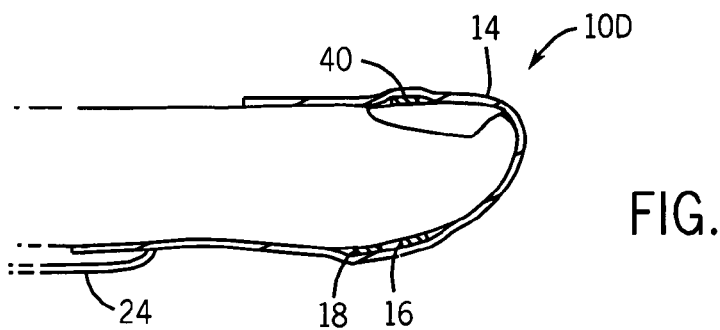
FIG. 10 is a view of the sensor of FIG. 9 applied to a patient's digit.
Figure 11:
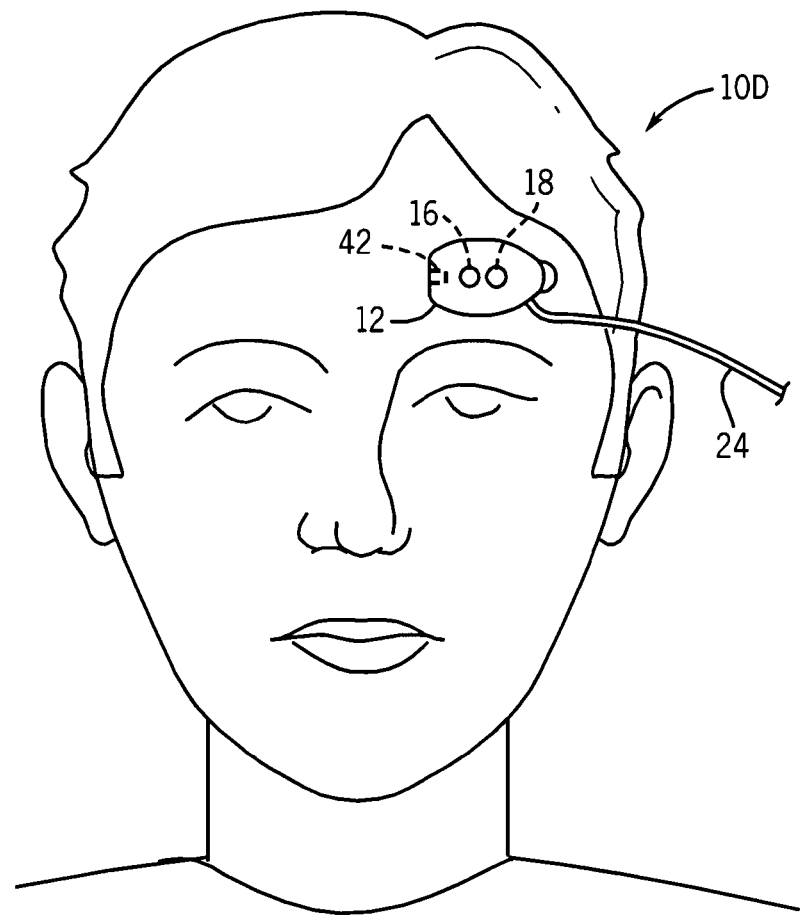
FIG. 11 is a view of the sensor of FIG. 9 applied to a patient's forehead after a portion of the sensor has been removed.

FIG. 9 illustrates a sensor 10D that includes an emitter 16 and detector 18 pair disposed on the detecting portion 12 of the sensor body 14. A removable portion 11 includes a secondary detector 40. Alternatively, the removable portion may include a secondary emitter (not shown) instead. When wrapped around a digit, as in FIG. 10, the sensor 10D may be adapted to operate in transmission mode. When the removable portion 11 including the secondary detector 40 is separated from the detecting portion 12, the sensor 10D is configured to operated in reflectance mode.

An operator may input the configuration of the sensor 10D into a medical monitor, or the sensor 10D may provide an electrical signal to a downstream medical device regarding the particular configuration of the sensor 10D. As shown, the sensor 10D may include an indicator circuit 42 that may be adapted to send an electrical signal through a wire lead 43 and cable 24 that may provide information about whether the sensor 10D is in a particular configuration. A downstream medical device may also determine the sensor configuration by running a test signal to the secondary detector 40. If the medical device receives no return signal from the secondary detector 40, the sensor 10D may be assumed to be in the forehead configuration.

In certain embodiments, the secondary detector 40 may be adapted to detect a different wavelength, or range of wavelengths, of emitted light. In such an embodiment, the configuration of the sensor may be associated with the physiological parameter being monitored. For example, the digit configuration may be adapted to monitor carboxyhemoglobin while the forehead configuration may be configured to monitor blood oxygen saturation.

Figure 12:
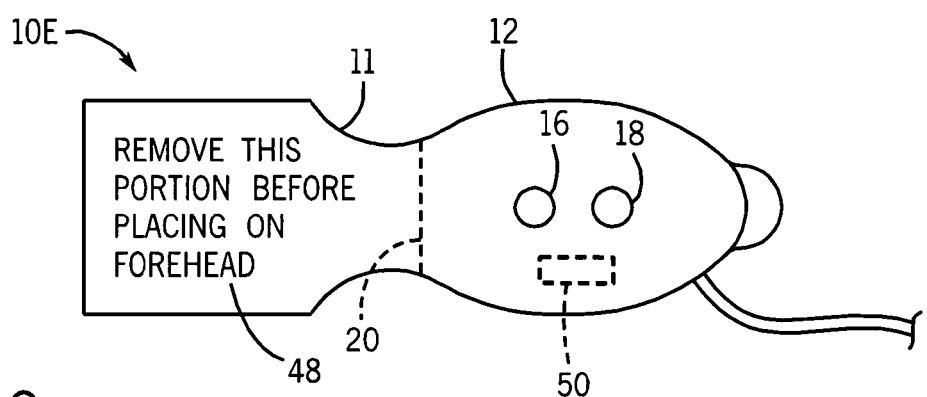
FIG. 12 illustrates an alternative multiple configuration medical sensor including a temperature sensor and indicia for designating a removable portion of the sensor.

FIG. 12 illustrates an alternate embodiment of a sensor 10E in which the removable portion 11 includes text 48 or other indicia, such as graphics or a raised or textured design, indicating that the portion 11 may be removed at perforation line 20 prior to placing the sensor 10E on a patient's forehead. Additionally, the sensor 10E may include a temperature sensor 50 disposed on the tissue-contacting surface of the portion 12 that includes the emitter 16 and the detector 18. The temperature sensor 50 may be adapted to provide an electrical signal to a downstream monitoring device related to the temperature of the tissue site being probed. A patient digit and a patient forehead may have characteristic skin temperatures due to differences in vascular structure and perfusion and thus may be differentiated by a signal sent by the temperature sensor 50 to a monitor. The temperature sensor may be any suitable sensor, including a thermistor.

Figure 13A:
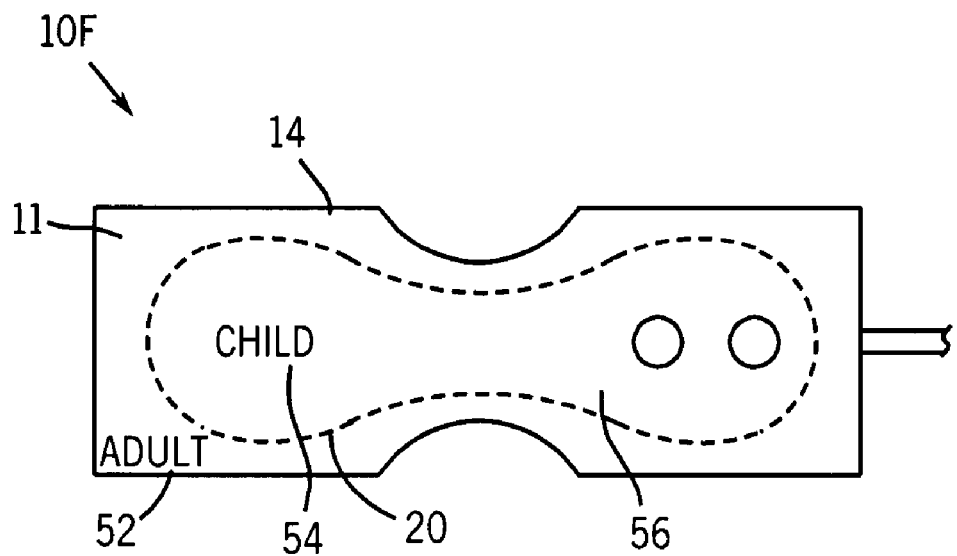
FIG. 13A illustrates an exemplary multiple configuration medical sensor that may be used in adult or pediatric populations with indicia for designating a removable portion of the sensor.
Figure 13B:
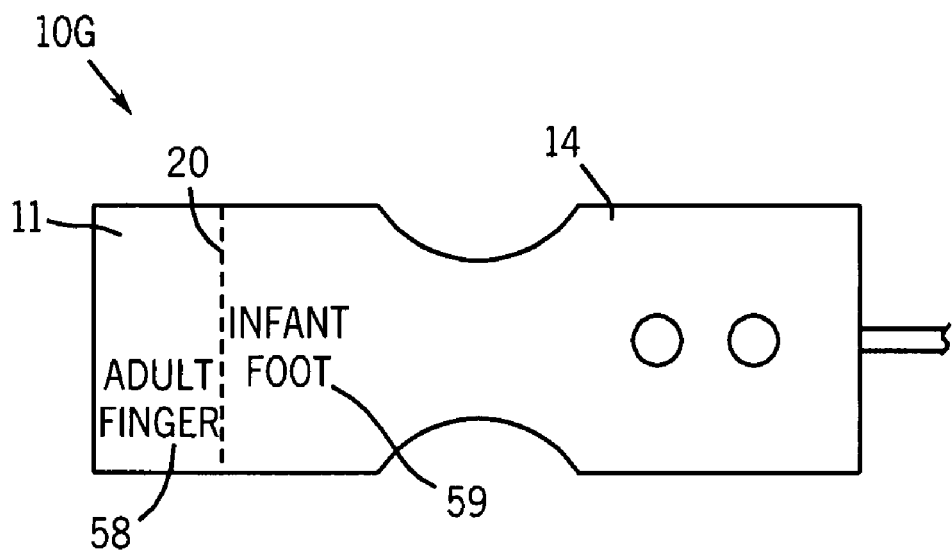
FIG. 13B illustrates an alternative multiple configuration medical sensor that may be used in adult or pediatric populations.

In certain embodiments, it may be useful to provide a sensor that may be configured for use on multiple patient populations, such as adult and pediatric populations. For example, a sensor may be adapted to have an "adult configuration" or a "child configuration." FIG. 13A illustrates a digit sensor 10F having a sensor body 14 that may be suitably sized for an adult digit. A perforation line 20 indicates a removable portion 11 that includes text 52, or other indicia, indicating that the portion 11 may be removed at perforation line 20 prior in order to resize the sensor 10F to conform to the digit of a child. As shown, the perforation line 20 may be disposed on the sensor body 14 to provide a sensor 10F of the same general shape in either the "adult configuration" or the "child configuration." The sensor 10F may also include additional text 54 to indicate the child-sized portion 56 of the sensor 10F. Additionally, the sensor 10F may also include any suitable indicator (not shown) that may be adapted to provide an electrical signal to a downstream monitoring device related to whether the removable portion 11 is present, thus indicating that the sensor 10F is in the "adult configuration." FIG. 13B illustrates a sensor 10G in which the removable portion 11 perforation line 20 is a simple straight line. Such a sensor 10G may provide certain operating advantages, as the removable portion 11 may be quickly and easily removed to configure the sensor in the "child configuration." Additionally, the perforation line 20 may be disposed on the sensor body 14 such that when the removable portion 11 is removed, the sensor 10G may be configured to conform to a neonate's foot or ankle. The sensor 10G may also include text 58 and 59, or other indicia, to inform the user which portion may be removed in order to configure the sensor 10G for use on an infant.

Figure 14:
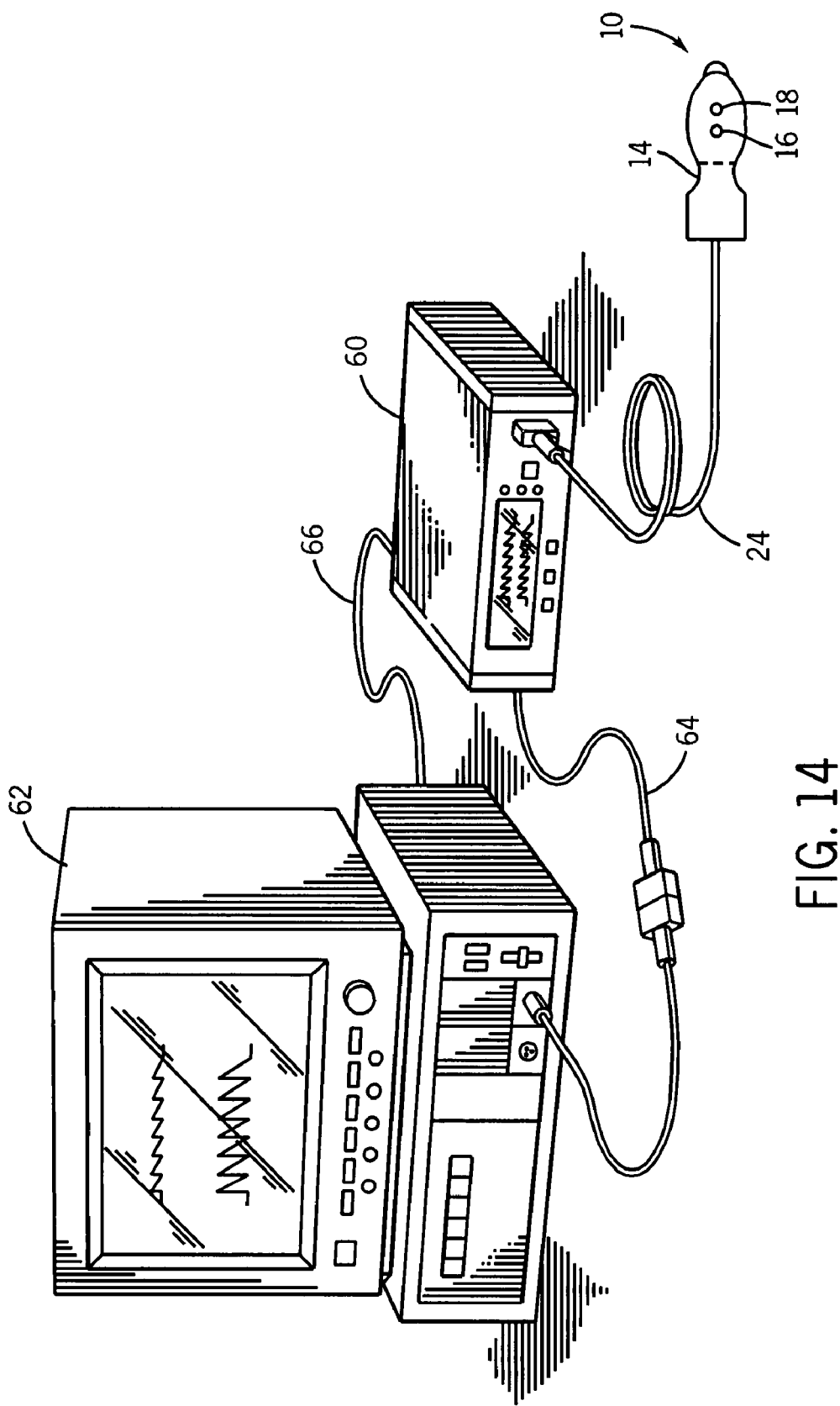
FIG. 14 illustrates a pulse oximetry system coupled to a multi-parameter patient monitor and a sensor according to embodiments of the present invention.

A sensor, illustrated generically as a sensor 10, may be used in conjunction with a pulse oximetry monitor 60, as illustrated in FIG. 14. It should be appreciated that the cable 24 of the sensor 10 may be coupled to the monitor 60 or it may be coupled to a transmission device (not shown) to facilitate wireless transmission between the sensor 10 and the monitor 60. The monitor 60 may be any suitable pulse oximeter, such as those available from Nellcor Puritan Bennett Inc. Furthermore, to upgrade conventional pulse oximetry provided by the monitor 60 to provide additional functions, the monitor 76 may be coupled to a multi-parameter patient monitor 62 via a cable 64 connected to a sensor input port or via a cable 66 connected to a digital communication port.

Figure 15:
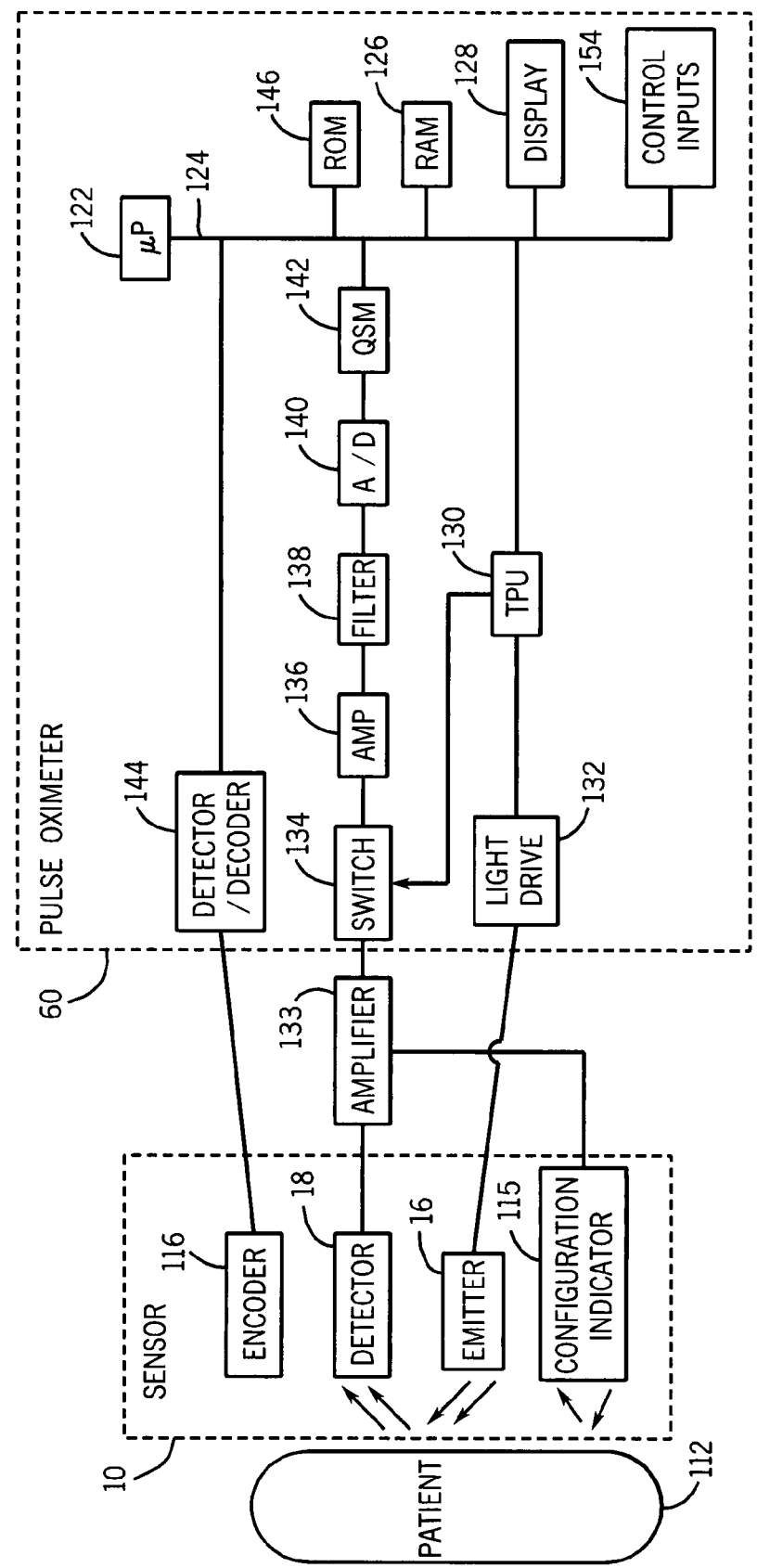
FIG. 15 is a block diagram of an exemplary pulse oximetry model connected to a sensor according to the present techniques.

FIG. 15 is a block diagram of one embodiment of a pulse oximeter that may be configured to implement the embodiments of the present invention. Light from emitter 16 passes into a blood perfused tissue 112, and is scattered and detected by detector 18. A sensor 10 containing an emitter 16 and a detector 18 may also contain an encoder 116 that provides signals indicative of the wavelength of light source 16 to allow the oximeter to select appropriate calibration coefficients for calculating oxygen saturation. The encoder 116 may, for instance, be a resistor. The sensor 10 may also include a configuration indicator 115 and may be configured to carry the configuration indicator signal to a monitor 60. The configuration indicator 115 may be an indicator circuit, pressure sensor, or temperature sensor as detailed herein, or any other indicator of sensor configuration.

The sensor 10 is connected to a pulse oximetry monitor 60. The monitor 60 includes a microprocessor 122 connected to an internal bus 124. Also connected to the bus are a RAM memory 126 and a display 128. A time processing unit (TPU) 130 provides timing control signals to light drive circuitry 132 which controls when the emitter 16 is illuminated, and if multiple light sources are used, the multiplexed timing for the different light sources. TPU 130 also controls the gating-in of signals from detector 18 through an amplifier 133 and a switching circuit 134. These signals are sampled at the proper time, depending upon which of multiple light sources is illuminated, if multiple light sources are used. The received signal from the detector 18 and the configuration indicator 115 may be passed through an amplifier 136, a low pass filter 138, and an analog-to-digital converter 140. The digital data is then stored in a queued serial module (QSM) 142, for later downloading to RAM 126 as QSM 142 fills up. In one embodiment, there may be multiple parallel paths of separate amplifier, filter and A/D converters for multiple light wavelengths or spectra received.

The monitor 60 may be configured to receive signals from the sensor 10 related to a physiological constituent and/or a configuration indicator 115 that may be processed by the monitor 60 to indicate a sensor configuration such as "digit configuration" or "forehead configuration." The monitor 60 may be configured to provide an indication about the sensor condition, such as an audio indicator, visual indicator or a display message, such as "DIGIT CONFIGURATION." Further, the monitor 60 may be configured to receive information about the configuration indicator 115 from a memory chip or other device, such as the encoder 116, which may be on the sensor 10 or the cable 24. Such a device may include a code or other identification parameter that may allow the monitor 60 to select an appropriate software or hardware instruction, which may include calibration coefficients for the emitter 16 and/or the detector 18, for processing the signal. For example, a monitor 60 may run an algorithm or code for processing the signal provided by the configuration indicator 115. For example, in certain embodiments, the processing algorithm may receive information that a circuit is either opened or closed, allowing for a simple binary determination of "digit configuration" or "forehead configuration," depending on the parameters of the particular configuration indicator 115. In other embodiments, a more complex algorithm may process a signal from a primary detector 18, or a secondary detector 40, or from both detectors, and may compare an increase or decrease in detected light to empirically-derived stored parameters to determine the sensor condition. In other embodiments, a signal may result in a hardware switch that may open or close a circuit, which may trigger the display 128 to include a sensor state message.

Based on the value of the received signals corresponding to the light received by detector 18, microprocessor 122 will calculate the oxygen saturation using various algorithms. These algorithms require coefficients, which may be empirically determined, corresponding to, for example, the wavelengths of light used. These are stored in a ROM 146. In a two-wavelength system, the particular set of coefficients chosen for any pair of wavelength spectra is determined by the value indicated by the encoder 116 corresponding to a particular light source in a particular sensor 10. In one embodiment, multiple resistor values may be assigned to select different sets of coefficients. In another embodiment, the same resistors are used to select from among the coefficients appropriate for an infrared source paired with either a near red source or far red source. The selection between whether the near red or far red set will be chosen can be selected with a control input from control inputs 154. Control inputs 154 may be, for instance, a switch on the pulse oximeter, a keyboard, or a port providing instructions from a remote host computer. Furthermore, any number of methods or algorithms may be used to determine a patient's pulse rate, oxygen saturation or any other desired physiological parameter.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of additional blood or tissue constituents, such as carboxyhemoglobin, met-hemoglobin, total hemoglobin, intravascular dyes, and/or water content. Rather, the invention is to cover all modifications, equivalents, and alternatives falling within the spirit and scope of the invention as defined by the following appended claims.

What is claimed is:

1. A sensor comprising:
   a conformable sensor body having a transmission configuration adapted to be applied to a first tissue site and a reflectance configuration adapted to be applied to a second tissue site;
   an emitter and a detector disposed on the sensor body; and
   a removable portion of the sensor body indicated by a marker, wherein when the removable portion is associated with the sensor body, the sensor body is in the transmission configuration and when the removable portion is removed from the sensor body, the sensor is in the reflectance configuration.

2. The sensor, as set forth in claim 1, wherein the sensor comprises at least one of a pulse oximetry sensor or a sensor for measuring a water fraction.

3. The sensor, as set forth in claim 1, wherein the emitter comprises at least one light emitting diode and wherein the detector comprises at least one photodetector.

4. The sensor, as set forth in claim 1, wherein the first tissue site comprises a digit and wherein the second patient site comprises a forehead.

5. The sensor, as set forth in claim 1, wherein the first tissue site comprises an adult tissue site and wherein the second patient site comprises a pediatric tissue site.

6. The sensor, as set forth in claim 1, comprising an indicator adapted to provide an electronic signal relating to the transmission configuration or the reflectance configuration.

7. The sensor, as set forth in claim 6, wherein the indicator comprises a breakable conductive element, a temperature sensor, a resistor, or a combination thereof.

8. The sensor, as set forth in claim 1, wherein the marker comprises a visible or tactile marker.

9. The sensor, as set forth in claim 1, wherein the marker comprises a perforated marker.

10. A sensor comprising:
    a sensor body having a first portion and a second portion that is removable from the first portion, wherein the sensor body comprises a single unitary structure prior to removal of the second portion, and wherein the first portion of the sensor body is adapted to be applied to a first tissue site in a reflectance configuration after removal of the second portion and the first portion and the second portion of the sensor body, when together, are adapted to be applied to a second tissue site in a transmission configuration; and
    an emitter and a detector disposed on the sensor body.

11. The sensor, as set forth in claim 10, wherein the sensor comprises at least one of a pulse oximetry sensor or a sensor for measuring a water fraction.

12. The sensor, as set forth in claim 10, wherein the emitter comprises at least one light emitting diode.

13. The sensor, as set forth in claim 10, wherein the detector comprises at least one photodetector.

14. The sensor, as set forth in claim 10, wherein the emitter and the detector are disposed on the first portion of the sensor body.

15. The sensor, as set forth in claim 14, comprising a second emitter or a second detector disposed on the second portion of the sensor body.

16. The sensor, as set forth in claim 10, comprising a perforated region disposed between the first portion and the second portion.

17. The sensor, as set forth in claim 10, comprising a marker disposed on the sensor body between the first portion and the second portion.

18. The sensor, as set forth in claim 10, comprising an indicator adapted to provide an electronic signal relating to the first configuration or the second configuration.

19. The sensor, as set forth in claim 18, wherein the indicator comprises a breakable conductive element, a temperature sensor, a resistor, or a combination thereof.

20. A sensor comprising:
a conformable sensor body having a first configuration adapted to be applied to a first tissue site and a second configuration adapted to be applied to a second tissue site, the first configuration being adapted to measure a first physiological parameter but not a second physiological parameter and the second configuration being adapted to measure a second physiological parameter but not the first physiological parameter; and
an emitter and a detector disposed on the sensor body.

21. The sensor, as set forth in claim 20, wherein the first physiological parameter comprises a blood oxygen saturation and the second physiological parameter comprises a water fraction.

22. The sensor, as set forth in claim 20, wherein the first physiological parameter comprises a blood oxygen saturation and the second physiological parameter comprises a carboxyhemoglobin or a methemoglobin.

23. The sensor, as set forth in claim 20, wherein the emitter comprises at least one light emitting diode and wherein the detector comprises at least one photodetector.

24. The sensor, as set forth in claim 20, wherein the first tissue site comprises a digit and wherein the second patient site comprises a forehead.

25. The sensor, as set forth in claim 20, wherein the first configuration and the second configuration comprise a reflectance-type sensor.

26. The sensor, as set forth in claim 20, wherein the first configuration comprises a transmission-type sensor and the second configuration comprises a reflectance-type sensor.

27. The sensor, as set forth in claim 20, wherein the sensor body comprises a perforated region adapted to define a removable portion of the sensor.

28. The sensor, as set forth in claim 27, wherein the indicator comprises a breakable conductive element, a temperature sensor, a resistor, or a combination thereof.

29. The sensor, as set forth in claim 20, comprising a marker disposed on the sensor body indicating a foldable or removable portion of the sensor.

30. The sensor, as set forth in claim 20, comprising an indicator adapted to provide an electronic signal relating to a first configuration or a second configuration.

31. A pulse oximetry system comprising:
a pulse oximetry monitor; and
a sensor adapted to be operatively coupled to the monitor, the sensor comprising:
a conformable sensor body having a first configuration adapted to be applied to a first tissue site and a second configuration adapted to be applied to a second tissue site; and
an emitter and a detector disposed on the sensor body;
a removable portion of the sensor body indicated by a marker, wherein when the removable portion is associated with the sensor body, the sensor body is in the first configuration and when the removable portion is removed from the sensor body, the sensor is in the second configuration; and
an indicator adapted to provide an electronic signal to the monitor relating to whether the sensor is in the first configuration or the second configuration.

32. The system, as set forth in claim 31, wherein the sensor comprises at least one of a pulse oximetry sensor or a sensor for measuring a water fraction.

33. The system, as set forth in claim 31, wherein the emitter comprises at least one light emitting diode and wherein the detector comprises at least one photodetector.

34. The system, as set forth in claim 31, wherein the first tissue site comprises a digit and wherein the second patient site comprises a forehead.

35. The system, as set forth in claim 31, wherein the first tissue site comprises an adult tissue site and wherein the second patient site comprises a pediatric tissue site.

36. The system, as set forth in claim 31, wherein the first configuration and the second configuration comprise a reflectance-type sensor.

37. The system, as set forth in claim 31, wherein the first configuration comprises a transmission-type sensor and the second configuration comprises a reflectance-type sensor.

38. The system, as set forth in claim 31, wherein the marker comprises a perforated region adapted to define the removable portion of the sensor.

39. The system, as set forth in claim 31, wherein the indicator comprises a breakable conductive element, a temperature sensor, a resistor, or a combination thereof.

40. The system, as set forth in claim 31, wherein the marker comprises a visible or tactile marker.

41. A method of operating a multi-configuration sensor comprising:
emitting light into a patient's tissue with an emitter disposed on a sensor body the sensor body being capable of a first configuration and a second configuration, the first configuration adapted to be applied to a first tissue site and the second configuration adapted to be applied to a second tissue site, and wherein removal or folding of a portion of the sensor body switches the sensor body from a first configuration to a second configuration;
detecting the light with a detector disposed on the sensor body; and
providing a signal indicative of a presence or absence of a removable portion of the sensor body.

42. The method, as set forth in claim 41, wherein providing the signal comprises measuring a temperature of the patient's tissue.

43. The method, as set forth in claim 41, wherein providing the signal comprises opening a circuit.

* * * * *